US012515052B2

(12) United States Patent
Spinale

(10) Patent No.: US 12,515,052 B2
(45) **Date of Patent: *Jan. 6, 2026**

(54) IMPLANTABLE DEVICE FOR TREATING MYOCARDIAL INFARCTION

(71) Applicant: MicroVide, LLC, Central, SC (US)

(72) Inventor: Francis G. Spinale, Mill Spring, NC (US)

(73) Assignee: MicroVide, LLC, Central, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/092,315

(22) Filed: Mar. 27, 2025

(65) Prior Publication Data

US 2025/0312606 A1 Oct. 9, 2025

Related U.S. Application Data

(62) Division of application No. 18/629,125, filed on Apr. 8, 2024, now Pat. No. 12,263,346.

(51) Int. Cl.

| | |
|---|---|
| ***A61N 1/36*** | (2006.01) |
| ***A61N 1/362*** | (2006.01) |
| ***A61N 1/365*** | (2006.01) |

(52) U.S. Cl.

CPC ....... *A61N 1/3627* (2013.01); *A61N 1/36521* (2013.01)

(58) Field of Classification Search

CPC .......................... A61N 1/3627; A61N 1/36521

See application file for complete search history.

(56) References Cited

U.S. PATENT DOCUMENTS

| | | | |
|---|---|---|---|
| 7,294,334 B1 | 11/2007 | Michal |
| 8,489,186 B2 | 7/2013 | Mukherjee |
| 8,771,714 B2 | 7/2014 | Spinale |
| 2001/0031986 A1 | 10/2001 | Hauck |
| 2013/0006318 A1 | 1/2013 | Weiss |
| 2021/0106249 A1 | 4/2021 | Schmidt |

FOREIGN PATENT DOCUMENTS

WO 2008/055225 A2 5/2008

OTHER PUBLICATIONS

Mukherjee R, et al., "Long-Term Localized High-Frequency Electric Stimulation Within the Myocardial Infarct: Effects on Matrix Metalloproteinases and Regional Remodeling," Circulation, Jul. 6, 2010, vol. 122, Issue 1, pp. 20-32.

(Continued)

*Primary Examiner* — Rex R Holmes

(57) ABSTRACT

An implantable system can treat a myocardial condition, for example a myocardial infarction region. The system can selectively apply stimulating electrical signals to the myocardial infarction region. The region can respond to the stimulating electrical signals by undergoing favorable therapeutic change, for example an increase in thickness of the region. The system can monitor electrical impedance of the region as an indicator of degree of regional therapeutic change or of regional therapeutic state. The monitoring results can guide or control the application of stimulating electrical signals. For example, the application of stimulating electrical signals can stop once the monitor detects a sufficient degree of favorable therapeutic change and can resume if the monitor detects a threshold degree of therapeutic regression.

20 Claims, 7 Drawing Sheets

(56) References Cited

OTHER PUBLICATIONS

Genau M., et al., "Institution of Localized High-Frequency Electrical Stimulation Targeting Early Myocardial Infarction: Effects on Left Ventricle Function and Geometry," The Journal of Thoracic and Cardiovascular Surgery, Aug. 2018, vol. 156, No. 2, pp. 568-575.
Aranyo J, et al., "Biophysical Tissue Characterization of Ventricular Tachycardia Substrate With Local Impedance Mapping to Predict Critical Sites," Journal of the American College of Cardiology: Clinical Electrophysiology, Jun. 2023, vol. 9, Issue 6, pp. 765-775.
Amoros-Figueras G, et al., "Recognition of Fibrotic Infarct Density by the Pattern of Local Systolic-Diastolic Myocardial Electrical Impedance," Frontiers in Physiology, Aug. 31, 2016, vol. 7, Art. 389.
Spinale, Francis G. and Deschamps, Anne, U.S. Appl. No. 60/855,419, entitled "Methods and System for Measurement of In Vivo Enzyme Activity," filed Oct. 31, 2006.

IMPLANTABLE DEVICE FOR TREATING MYOCARDIAL INFARCTION

CROSS-REFERENCE TO RELATED APPLICATIONS

This application claims priority to and is a divisional application of U.S. patent application Ser. No. 18/629,125 filed Apr. 8, 2024 in the name of Francis G. Spinale, entitled "Systems and Methods for Treating Myocardial Conditions," and assigned an issue date of Apr. 1, 2025 as U.S. Pat. No. 12,263,346, the entire contents of which are hereby incorporated herein by reference. The entire contents of said U.S. patent application Ser. No. 18/629,125 are hereby incorporated herein by reference.

STATEMENT REGARDING FEDERALLY SPONSORED RESEARCH OR DEVELOPMENT

This invention was made with government support under R42HL112519 awarded by the U.S. National Institutes of Health. The government has certain rights in the invention.

TECHNICAL FIELD

Embodiments of the technology relate generally to treating myocardial conditions, such as producing favorable therapeutic change of a myocardial infarction region of a myocardium, and more particularly to applying stimulating electrical signals to the region and monitoring for change in electrical impedance of the region as indicative of degree of therapeutic change.

BACKGROUND

In many respects, conventional technologies underserve treating myocardial conditions. For instance, need exists for a capability to monitor state of a myocardium during treatment of the myocardium. Need further exists for a capability to produce a favorable therapeutic change in a myocardial infarction region of the myocardium under support of monitoring therapeutic state of the region or monitoring the region for therapeutic change.

Need further exists for a capability to activate fibroblasts in or associated with the myocardial infarction region of the myocardium under support of monitoring the region for fibroblast activation or an indicator thereof. Need further exists for a capability to balance between matrix metalloproteinases and tissue inhibitors of metalloproteinases in or associated with the myocardial infarction region under support of monitoring the region for such balance or an indicator thereof. Need further exists for a capability to reduce interstitial matrix metalloproteinase activity in or associated with the myocardial infarction region under support of monitoring the region for such activity or an indicator thereof. Need further exists for a capability to increase collagen content in or associated with the myocardial infarction region under support of monitoring the region for collagen content or an indicator thereof. Need further exists for a capability to increase regional stiffness of or associated with the myocardial infarction region under support of monitoring the region for stiffness or an indicator thereof. Need further exists for a capability to improve tensile strength in or associated with the myocardial infarction region under support of monitoring the region for tensile strength or an indicator thereof. Need further exists for a capability to improve compliance of the myocardial infarction region or compliance associated with the region under support of monitoring the region for compliance or an indicator thereof. Need further exists for a capability to reduce size of the myocardial infarction region under support of monitoring size of the region or an indicator thereof. Need further exists for a capability to prevent thinning of the myocardial infarction region or thinning associated with the region under support of monitoring thinning of the region or an indicator thereof. Need further exists for a capability to arrest progressive thinning of the myocardial infarction region or associated with the region under support of monitoring the region for thinning or an indicator thereof. Need further exists for a capability to thicken the myocardial infarction region under support of monitoring thickness of the region or an indicator thereof. Need further exists for a capability to favorably modify left ventricular remodeling following a myocardial infarction under support of monitoring for favorable modification or an indicator thereof.

The aforementioned needs are representative rather than exhaustive. A technology addressing one or more of the needs discussed above, or some related deficiency in the art, would benefit cardiology and those suffering from cardiological maladies. As will be appreciated by those having skill in the art, the disclosure provided herein includes written description containing clear, exact terms to enable carrying out embodiments meeting the foregoing needs.

SUMMARY

Myocardial conditions can be treated. In some aspects of the disclosure, a treated myocardial condition can comprise a myocardial infarction region of a myocardium. In some aspects of the disclosure, the treated myocardial condition can comprise a myocardial lesion of the myocardium.

In some aspects of the disclosure, a system for treating the myocardial condition can comprise a stimulator. In some aspects, the stimulator can apply stimulating electrical signals to the myocardium via one or more electrical leads to produce favorable therapeutic change. For instance, the stimulator can selectively apply stimulating electrical signals to the myocardial infarction region to produce favorable therapeutic change of the myocardial infarction region. In some aspects, the stimulator can comprise an electrical tissue stimulator.

In some aspects of the disclosure, the system for treating the myocardial condition can comprise a single bipolar electrical lead that is placed in a central portion of the myocardial infarction region. With the single bipolar electrical lead centrally placed, electrical propagation can disburse within the myocardial infarction region in a waveform pattern. In some subaspects, electrical propagation can remain confined or substantially confined to the myocardial infarction region. In some subaspects, electrical propagation can avoid or substantially avoid viable tissue of the myocardium. In some subaspects, electrical propagation may not enter viable tissue, or may not measurably enter viable tissue. In some subaspects, the system provides an electrically isolated signal to the myocardial infarction region which does not capture viable cardiac muscle.

In some aspects of the disclosure, the favorable therapeutic change can comprise, for example, activation of fibroblasts in the myocardial infarction region, balancing between matrix metalloproteinases and tissue inhibitors of metalloproteinases in the myocardial infarction region, a reduction of interstitial matrix metalloproteinase activity in the myocardial infarction region, an increase in collagen content in the myocardial infarction region, an increase in regional stiffness of the myocardial infarction region, improvement in tensile strength of the myocardial infarction region, improvement in compliance of the myocardial infarction region, size reduction of the myocardial infarction region, prevention of thinning of the myocardial infarction region, arresting progressive thinning of the myocardial infarction region, thickening of the myocardial infarction region, or favorably modifying left ventricular remodeling following a myocardial infarction, or a combination thereof (not an exhaustive list).

In some aspects of the disclosure, the system can comprise a monitor. In some aspects, the monitor can monitor therapeutic change of the myocardium. In some aspects, the monitor can monitor electrical impedance of the myocardium as an indicator of therapeutic change or therapeutic state of myocardial tissue. The therapeutic change can be favorable and can be attributable to stimulating electrical signals applied by the stimulator. The monitor can, for example, apply monitoring electrical signals to the myocardial infarction region via one or more electrical leads. In some aspects, the monitor can assess or determine electrical impedance of the myocardial infarction region by processing the monitoring electrical signals to determine how the signals interact with the myocardial infarction region. In some aspects, a decrease in electrical impedance can indicate favorable therapeutic change and an increase in electrical impedance can indicate unfavorable therapeutic change.

In some aspects of the disclosure, the monitor can support or provide feedback for the stimulator. In some aspects, the application of stimulating electrical signals can be controlled or guided according to monitored therapeutic change of the myocardium, such as favorable therapeutic change of the myocardial infarction region. For example, the application of stimulating electrical signals can be stopped once the monitor detects an electrical impedance of the myocardial infarction region that indicates sufficient favorable therapeutic change has occurred. In some aspects, the monitor can continue monitoring electrical impedance of the myocardial infarction region after application of stimulating electrical signal has been stopped. For example, if the monitor detects a change in electrical impedance that indicates or is attributable to regression of the favorable therapeutic change, then the application of stimulating electrical signals can resume.

In some aspects of the disclosure, the system can be implanted and can operate autonomously. For example, the implanted system can autonomously control the application of stimulating electrical signals based on therapeutic change as monitored by the system.

In some aspects of the disclosure, the system can be implanted and can operate semi-autonomously or with some human input or control. In some aspects, the implanted system can comprise a capability for transmitting and receiving wireless information. For example, the system can send monitored information about therapeutic changes to a human medical practitioner. The medical practitioner can review the information and send wireless commands to the implanted system, for instance instructing the system to stop or otherwise change the application of stimulating electrical signals.

The foregoing discussion about treating myocardial conditions is for illustrative purposes only. Various aspects of the present disclosure may be more clearly understood and appreciated from a review of the following text and by reference to the associated drawings and the claims that follow. This Summary does not intend to be exhaustive, nor does it intend to enumerate each and every aspect of the disclosure. Other aspects, systems, methods, features, advantages, and objects of the present disclosure will become apparent to those with skill in the art upon examination of the following text and the accompanying drawing figures. It is intended that all such aspects, systems, methods, features, advantages, and objects are to be included within this description and covered by this paper and by the appended claims.

Figure 1A:
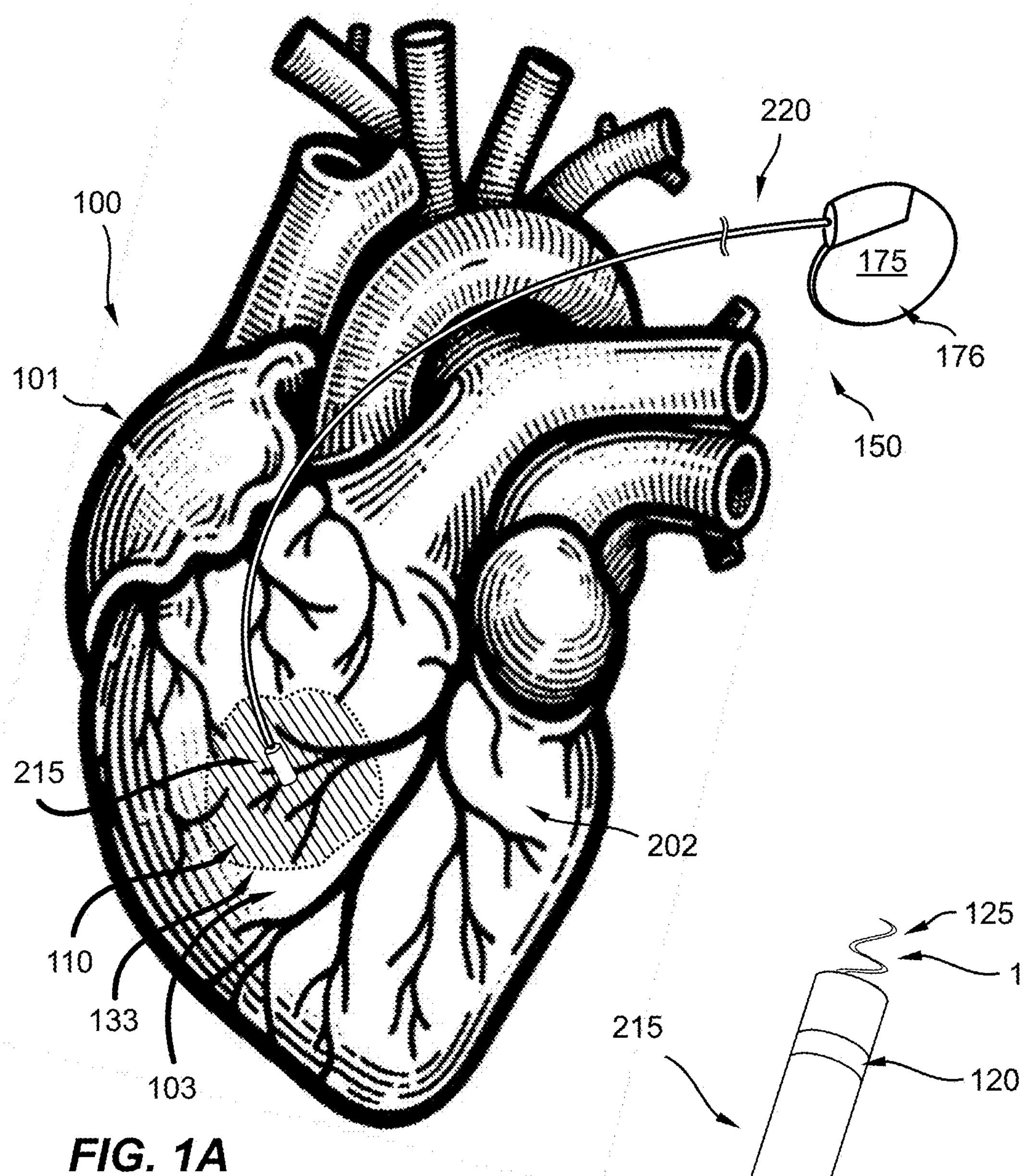
FIGS. 1A and 1B (collectively FIG. 1) are illustrations of a system for treating a myocardial condition in accordance with some example embodiments of the disclosure.

Many aspects of the disclosure can be better understood with reference to these figures. The elements and features shown in the figures are not necessarily to scale, emphasis being placed upon clearly illustrating principles of example embodiments of the disclosure. Moreover, certain dimensions and features may be exaggerated to help visually convey such principles. In the figures, reference numerals often designate like or corresponding, but not necessarily identical, elements throughout the several views.

DETAILED DESCRIPTION OF EXAMPLE EMBODIMENTS

The technology will be discussed more fully below with reference to the figures, which provide additional information regarding representative or illustrative embodiments of the disclosure. The present technology can be embodied in many different forms and should not be construed as limited to the embodiments set forth herein; rather, these embodiments are provided so that this disclosure will be thorough and complete, and will fully convey the scope of the technology to those having ordinary skill in the art. Furthermore, all "examples," "embodiments," and "example embodiments" provided herein are intended to be non-limiting and among others supported by representations of the disclosure.

Those of ordinary skill in the art having benefit of this disclosure will be able, without undue experimentation, to combine compatible elements and features that are described at various places in this written description, which includes text and illustrations. That is, the illustrations and specification are organized to facilitate practicing numerous combinations, such as by combining an element of one illustrated embodiment with another element of another illustrated embodiment or by combining a feature disclosed in an early paragraph of the specification with another feature disclosed in a later paragraph of the specification.

This document includes sentences, paragraphs, and passages (some of which might be viewed as lists) disclosing alternative components, elements, features, functionalities, usages, operations, steps, etc. for various embodiments of the disclosure. Unless clearly stated otherwise, all such lists, sentences, paragraphs, passages, and other text are not exhaustive, are not limiting, are provided in the context of describing representative examples and variations, and are among others supported by various embodiments of the disclosure. Accordingly, those of ordinary skill in the art having benefit of this disclosure will appreciate that the disclosure is not constrained by any such lists, examples, or alternatives. Moreover, the inclusion of lists, examples, embodiments, and the like (where provided as deemed beneficial to readers) may help guide those of ordinary skill in practicing many more implementations and instances that embody the technology without undue experimentation, all of which are intended to be within the scope of the claims.

This disclosure includes figures and discussion in which features and elements of certain embodiments may be organized into what might be characterized as functional blocks, units, subsystems, or modules. And, certain processes and methods may be organized into blocks or into steps. Such organization is intended to enhance readership and to facilitate teaching readers about working principles of the technology and about making and using an abundance of embodiments of the disclosure. The organization is not intended to force any rigid divisions or partitions that would limit the disclosure. In practice, the flexibility of the technology and the depth of this disclosure supports dispersing or grouping functionalities, elements, and features in many different ways. The inclusion of an element or function in one block, unit, module, or subsystem verses another may be substantially arbitrary in many instances, with the divisions being soft and readily redrawn using the teaching provided herein in combination with ordinary skill. Accordingly, functional blocks, modules, subsystems, units, and the like can be combined, divided, repartitioned, redrawn, moved, reorganized, or otherwise altered without deviating from the scope and spirit of the disclosure. This is not to say that, nor will it support a conclusion that, any disclosed organizations or combinations are not novel, are not inventive, or are obvious.

Certain steps in the processes and methods disclosed or taught herein, may naturally need to precede others to achieve desirable functionality. However, the disclosure is not limited to the order of the described steps if such order or sequence does not adversely alter functionality to the extent of rendering the technology inoperable or nonsensical. That is, it is recognized that some steps of a process or method may be performed before or after other steps or in parallel with other steps without departing from the scope and spirit of the disclosure.

In some instances, a process or method (for example that entails using, making, or practicing) may be discussed with reference to a particular illustrated embodiment, application, or environment. For instance, a flowchart may reference or be discussed with reference to a specific figure. Those of skill in the art will appreciate that any such references are by example and are provided without limitation. Accordingly, the disclosed processes and methods can be practiced with other appropriate embodiments supported by the present disclosure and in other appropriate applications and environments. Moreover, one of ordinary skill in the art having benefit of this disclosure will be able to practice many variations of the disclosed and flowcharted methods and processes as may be appropriate for various applications and embodiments.

The term "couple," as used herein, generally refers to joining, linking, connecting, or associating something with something else. When two things couple or something couples with something else, they may directly couple or indirectly couple via another, intervening component, element, or module. A first component may couple to or with a second component via the first component comprising the second component. Moreover, a first thing can couple to or with a second thing without physical contact, for example optically or via sound. The term can thus be read with a plain and ordinary meaning.

The term "coupled," as used herein in a context of a first thing being coupled to or with a second thing, generally refers to the first thing being joined, linked, connected, or associated to or with the second thing. When something is coupled to or with something else, they may be directly coupled or indirectly coupled via another, intervening component, element, or module. Moreover, a first component may be coupled to or with a second component via the first component comprising the second component. A first thing can be coupled to or with a second thing without physical contact, for example optically or via sound. The term can thus be read with a plain and ordinary meaning.

The term "electrically coupled," as used herein in the context of two things being electrically coupled, generally refers to the two being things coupled in a way that allows, supports, or facilitates transfer, flow, or propagation, of electricity. An electrical circuit can comprise two components that are electrically coupled to or with one another even though the circuit is not connected to a power source and an open switch separates the two components; as once the power source is connected and the switch is closed, electricity can flow. As another example, suppose an electrical source has a female connector and an electrical lead has a male connector that is configured to mate with the female connector. Further suppose the electrical source and the electrical lead are supplied with the electrical source and the electrical lead disconnected and individually packaged. The electrical source and the electrical lead would be electrically coupled to one another in their disconnected, separately packaged state; as once the female and male connectors are connected together or mated, electricity can flow.

The term "operably coupled," as used herein in the context of two things being operably coupled, generally refers to the two things being coupled in a way that allows, supports, or facilitates something to work or operate. The term can thus be read with an ordinary and customary meaning.

When the terms "a" or "an" are used herein, one or more is to be generally understood, except when more than one would be nonsensical in context or would adversely alter functionality to the extent of rendering technology inoperable.

As one of ordinary skill in the art will appreciate, each of the terms "approximate" and "approximately," as used herein, provides an industry-accepted tolerance for the corresponding term modified. Such industry-accepted tolerances range from less than one percent to ten percent and correspond to, but are not limited to, component values, signal levels, process variations, operational targets, and manufacturing tolerance.

The terms "substantial" and "substantially," as used herein, are words of degree accommodating deviations that a skilled artisan would recognize as unintentional deviation from a target value or as inconsequential.

In each instance in which a number is disclosed for an embodiment, it is intended that approximately the number is disclosed for an embodiment and that substantially the number is disclosed for an embodiment. For example, if the specification discloses an embodiment comprising a length of 1.0 millimeter, it will be understood that a disclosed embodiment comprises a length of approximately 1.0 millimeter and that a disclosed embodiment comprises a length of substantially 1.0 millimeter.

In each instance in which a range of numbers is disclosed for an embodiment, it is intended that approximately the range of numbers is disclosed for an embodiment and that substantially the range of numbers is disclosed for an embodiment. For example if the specification discloses an embodiment comprising a length in a range of 1.0 to 2.0 millimeters, it will be understood that a disclosed embodiment comprises a length in an approximate range of 1.0 to 2.0 millimeters. Further, in this example, a disclosed embodiment comprises a length in a range of approximately 1.0 millimeter to approximately 2.0 millimeters. Further, in this example, a disclosed embodiment comprises a length in a substantial range of 1.0 to 2.0 millimeters. Further, in this example, a disclosed embodiment comprises a length in a range of substantially 1.0 millimeter to substantially 2.0 millimeters.

As will be appreciated by those of skill in the art, unless clearly specified otherwise, the values provided herein are intended to reflect commercial design practices or nominal manufacturing targets. For example, what may be described or specified as having a dimension of one millimeter or 1.0 mm, may deviate from one millimeter or 1.0 mm when implemented in a commercial product due to fabrication error, warpage, or customary tolerances.

The term "stimulate," as used herein, generally refers to encouraging, causing, triggering, or activating something to grow, develop, change, improve, become active, or become more active. The term can thus be read with a plain and ordinary meaning.

The term "stimulator," as used herein, generally refers to an apparatus or system that stimulates. The term can thus be read with a plain and ordinary meaning.

The term "electrical stimulator," as used herein, generally refers to a stimulator that stimulates using electricity. The term can thus be read with an ordinary and customary meaning.

The term "electrical tissue stimulator," as used herein, generally refers to an electrical stimulator that stimulates tissue, an organ, or a portion of an organ using electricity. The term can thus be read with an ordinary and customary meaning.

The term "monitor," as used herein as a noun, generally refers to an apparatus or system that monitors. For example, a monitor may monitor, observe, detect, measure, determine, assess, characterize, or sense a characteristic or parameter of biological tissue. The term can thus be read with a plain and ordinary meaning.

The term "electrical impedance monitor," as used herein, generally refers to a monitor that monitors electrical impedance. For example, an electrical impedance monitor may monitor, observe, detect, measure, determine, assess, characterize, or sense electrical impedance of biological tissue. The term can thus be read with an ordinary and customary meaning.

The term "tissue impedance monitor," as used herein, generally refers to a monitor that monitors electrical impedance of tissue, an organ, or a portion of an organ. The term can thus be read with an ordinary and customary meaning.

The term "therapeutic change monitor," as used herein, generally refers to a monitor that monitors therapeutic change of tissue.

The term "instrument," as used herein, generally refers to a system designed for a purpose that involves precision operation. The term can thus be read with a plain and ordinary meaning.

The term "myocardial lesion," as used herein, generally refers to myocardial tissue (or a region of a myocardium) that is diseased or injured or that has undergone a change in structure or function due to injury or disease. A specific example of a myocardial lesion would be a fibrotic region of the myocardium which occurs after a myocardial infarction. The term lesion does not preclude a need to treat several lesion areas of the heart.

The written description (comprising text and figures) of the present patent application includes content that is incorporated by reference and content that has not been incorporated by reference (i.e., content that is written directly into the specification and figures as originally filed at the U.S. Patent Office). In the event that inconsistency exists between the incorporated-by-reference content and the not-incorporated-by-reference content with respect to usage, interpretation, meaning, definition, or construction of a term, then the not-incorporated-by-reference content shall dictate usage, interpretation, meaning, definition, or construction of the term.

Moving to the drawings, FIGS. 1, 2, 3, 4, 5, 6, 7, and 8 describe representative features of some example systems for treating myocardial conditions and monitoring myocardial response to treatment. As further discussed below, FIGS. 1, 2, and 3 respectively illustrate three example embodiments of a system for treating a myocardial condition, such as a myocardial infarction region.

Figure 1B:
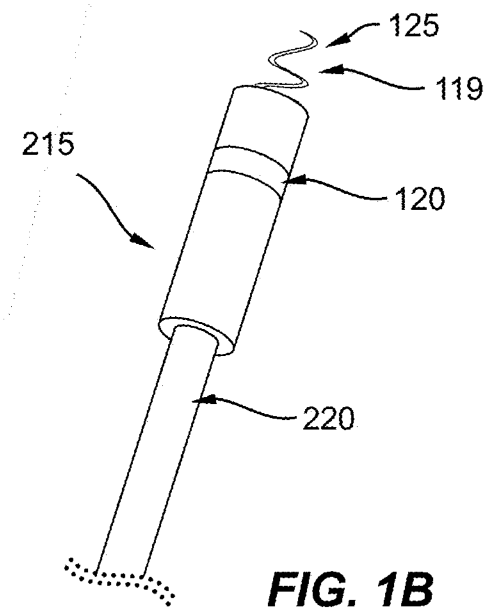

Turning now to FIGS. 1A and 1B, these figures illustrate an example system 150 for treating a myocardial condition according to some embodiments of the disclosure. FIG. 1A illustrates the system 150 in an example operating environment. FIG. 1B illustrates an example distal end 215 of an example bipolar electrical lead 220 that the system 150 comprises.

Figure 3:
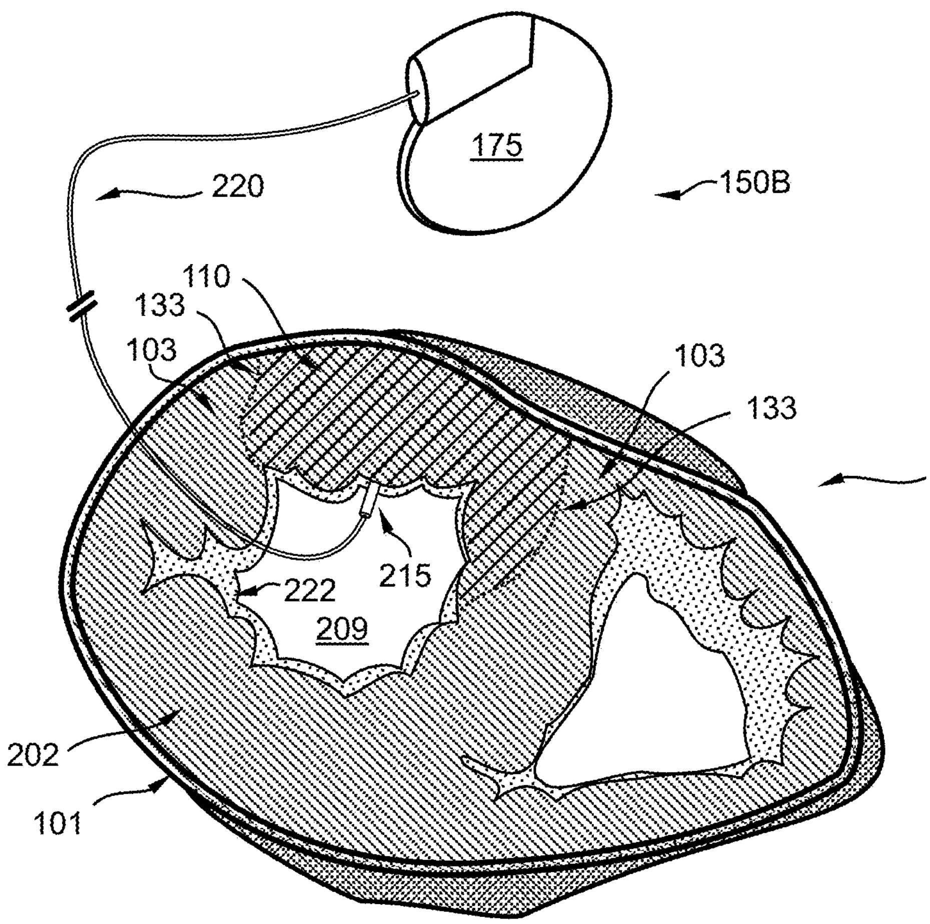
FIG. 3 is an illustration of a system for treating a myocardial condition in accordance with some example embodiments of the disclosure.

In the example application of FIG. 1, the myocardial condition comprises a myocardial infarction region 110 of a heart 100 that the system 150 is configured to treat. As shown in the cross sectional view of the heart 100 that FIG. 3 illustrates, the myocardial infarction region 110 extends into the myocardium 202, and the myocardium 202 comprises the myocardial infarction region 110. As illustrated, a boundary 133 exists between injured, hypoxic tissue of the myocardial infarction region 110 and viable, normoxic myocardial tissue 103. In some example embodiments, the boundary 133 comprises a border zone that exhibits an oxygen gradient.

The myocardial infarction region 110 comprises an example embodiment of a myocardial lesion that embodiments of the system 150 can treat. In some example embodiments, the system 150 can treat a myocardial condition or a myocardial lesion that comprises a fibrotic lesion, an arrhythmia, or an ischemic area of the myocardium. In some example embodiments, the system 150 can treat a myocardial condition or a myocardial lesion that comprises a coronary lesion. In some example embodiments, the system 150 can treat a myocardial condition or a myocardial lesion that comprises myocardial ischemia. In some example embodiments, the system 150 can treat a myocardial condition or a myocardial lesion that comprises cardiac arrhythmia. In some example embodiments, the system 150 can treat a myocardial condition or a myocardial lesion that comprises myocardial ischemia with infarction. In some example embodiments, the system 150 can treat a myocardial condition or a myocardial lesion that comprises myocardial ischemia without infarction. In some example embodiments, the system 150 can treat a myocardial condition or a myocardial lesion that comprises scarring. In some example embodiments, the system 150 can treat a myocardial condition or a myocardial lesion that comprises myocardial infarction. In some example embodiments, the system 150 can treat a myocardial condition or a myocardial lesion that comprises one or more cardiac electrical abnormalities, such as arrhythmias. In some example embodiments, the system 150 can treat a myocardial condition or a myocardial lesion that comprises acute coronary syndrome. In some example embodiments, the system 150 can treat other myocardial conditions or myocardial lesions.

In some example embodiments, the system 150 can treat subjects having, or at risk of developing, a myocardial condition. In some example embodiments, the system 150 can treat subjects having or at risk of having acute coronary syndrome or a coronary artery bypass graft. In some example embodiments, the system 150 can treat subjects predisposed to cardiac ischemia or to myocardial lesions that are not ischemic. Treated subjects can comprise humans. Treated subjects can comprise non-human animals. Treated subjects can comprise human and veterinary patients.

As illustrated by FIG. 1A, the system 150 comprises an example instrument 175 from which the bipolar electrical lead 220 extends. The instrument 175 comprises electrical circuitry for generating and analyzing electricity transmitted over the bipolar electrical lead 220 as further discussed below. The electrical circuitry is enclosed in an implantable housing 176. As illustrated by FIG. 1A, the instrument 175 comprises an example form factor that resembles or is consistent with an implantable pulse generator of a typical, commercially available pacemaker. In some example embodiments, the implantable housing 176 of the instrument 175 comprises a housing of a commercially available pacemaker of Medtronic Plc of Minneapolis, Minnesota; Boston Scientific Corporation of Marlborough, Massachusetts; Abbott Laboratories of Abbott Park, Illinois; or another suitable supplier.

The system 150 comprises an example embodiment of an implantable system. FIG. 1 illustrates the system 150 as applied in an example epicardial implantation, which is typically a surgical procedure that is conducted in an operating room and that involves accessing the heart 100 via an abdominal incision. Implantation entails disposing the distal end 215 of the bipolar electrical lead 220 adjacent, adjoining, or penetrating the heart 100.

As illustrated, the distal end 215 is affixed or fastened to an epicardium 101 and a myocardium 202 of the heart 100. More specifically, the distal end 215 is fastened to a central region of the myocardial infarction region 110 that the myocardium 202 comprises. The distal end 215 of the bipolar electrical lead 220 comprises a fastener 119 that, in implantation, screws through the epicardium 101 and into the myocardium 202. (See FIG. 3A for a representative cross sectional view of the heart 100 illustrating the epicardium 101 and the myocardium 202.) Thus, a single bipolar electrical lead 220 distally affixes or fastens to the myocardial infarction region 110 via the fastener 119.

As illustrated by FIG. 1B, the fastener 119 at the distal end 215 of the bipolar electrical lead 220 comprises a cathode electrode 125. The distal end 215 of the bipolar electrical lead 220 further comprises an anode electrode 120 longitudinally spaced from the cathode electrode 125. In some example embodiments, the bipolar electrical lead 220 comprises a commercially available lead of a commercially available pacemaker of Medtronic Plc, Boston Scientific Corporation, Abbott Laboratories, or another suitable supplier.

In operation, the instrument 175 produces stimulating electrical signals that transmit over the bipolar electrical lead 220 and flow between the cathode electrode 125 and the anode electrode 120. With the system 150 implanted as illustrated by FIG. 1A, electricity propagates through the myocardial infarction region 110 as the electricity flows between the pair of electrodes 120, 125.

In the illustrated implantation, the distal end 215 of the bipolar electrical lead 220 is centrally disposed at an exterior surface of the myocardial infarction region 110. That is, the fastener 119 and the cathode electrode 125 are positioned in a central portion of the myocardial infarction region 110. With the distal end 215 of the bipolar electrical lead 220 so placed, propagation of stimulating electrical signals can disburse within the myocardial infarction region 110 in a waveform pattern. In some example embodiments, electrical propagation remains confined or substantially confined to the myocardial infarction region 110. Stimulating electrical signals can avoid or substantially avoid viable tissue 103 of the myocardium 202. For example, stimulating electrical signals may not enter viable tissue 103, or may not measurably enter viable tissue 103. The system 150 can provide an electrically isolated signal to the myocardial infarction region 110 which does not capture viable cardiac muscle 103. Accordingly, electrical stimulation can be limited, or substantially limited, to within the boundary 130 of the myocardial infarction region 110.

Figure 2A:
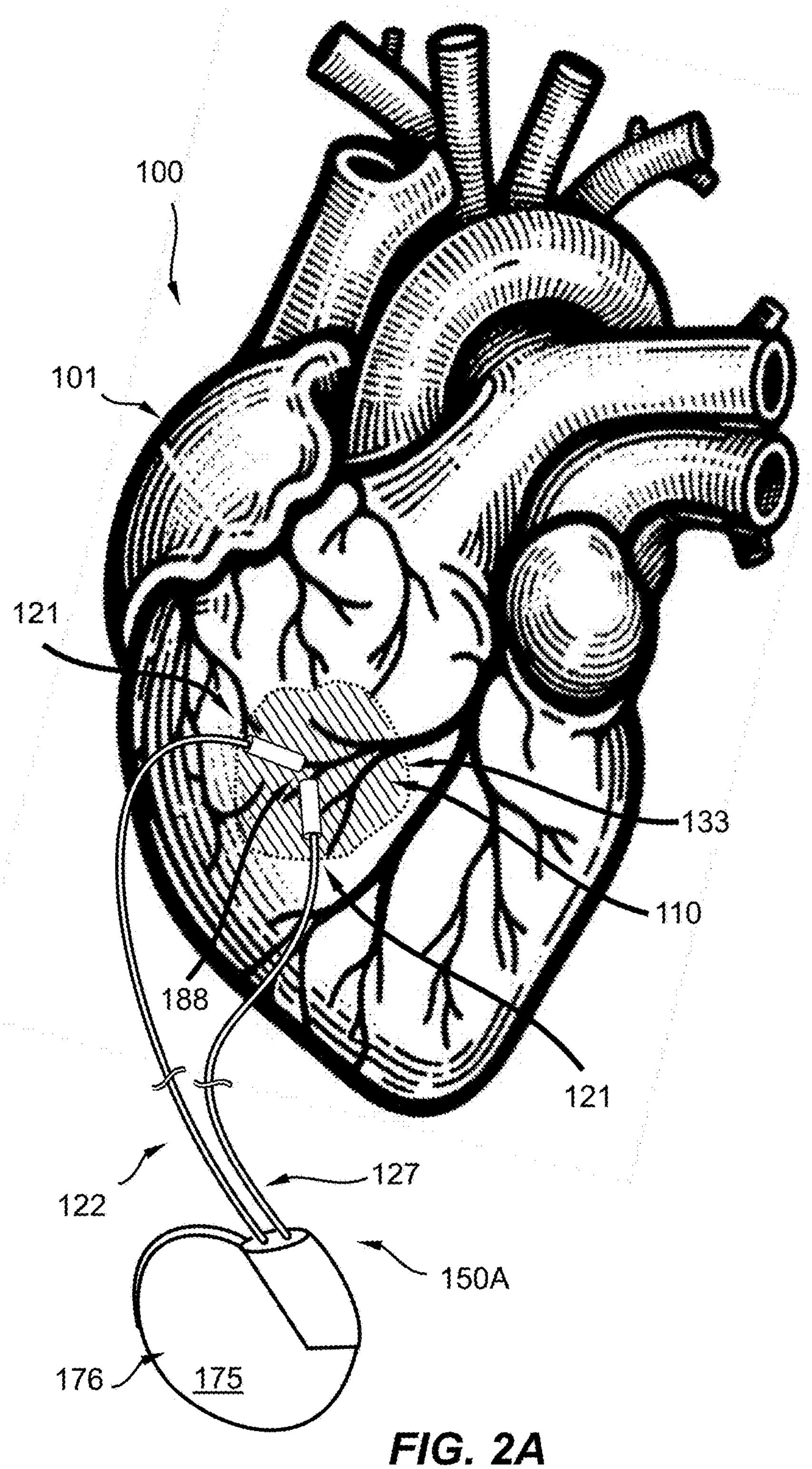
FIGS. 2A, 2B, and 2C (collectively FIG. 2) are illustrations of a system for treating a myocardial condition in accordance with some example embodiments of the disclosure.
Figure 2B:
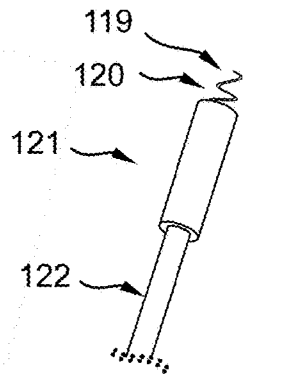
Figure 2C:
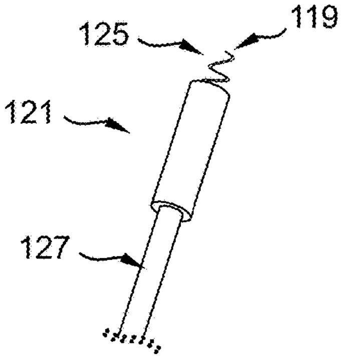

Turning now to FIGS. 2A, 2B, and 2C, these figures illustrate an example system 150A for treating a myocardial condition according to some embodiments of the disclosure. FIG. 2A illustrates the system 150A in an example operating environment. FIGS. 2B and 2C respectively illustrate a distal end 121 of an example anode electrical lead 122 and a distal end 121 an example cathode electrical lead 127 that the system 150A comprises.

The system 150A comprises an example embodiment of an implantable system. The system 150A is compatible with epicardial implantation, as discussed above with reference to FIG. 1. FIG. 2A illustrates the system 150A as configured in a representative epicardial implantation.

Whereas the example system 150 of FIG. 1 comprises a single bipolar lead 220 connected to and extending from the instrument 175, the example system 150A of FIG. 2 comprises two unipolar leads 122, 127 connected to and extending from an instrument 175. In some example embodiments, the instrument 175 of the system 150A of FIG. 2 differs from the instrument 175 of the system 150 of FIG. 1 in configuration of lead connection. Accordingly, the instruments 175 of the two example systems 150, 150A can otherwise comprise like or substantially equivalent circuity and functionality.

In the illustrated example of FIG. 2, the fastener 119 disposed at the distal end 121 of the anode electrical lead 122 comprises an anode electrode 120. And, the fastener 119 disposed at the distal end 121 of the cathode electrical lead 127 comprises a cathode electrode 125. Accordingly, the system 150A comprises two unipolar leads 122, 127 for transmitting stimulating electrical signals through the myocardial infarction region 110. In some example embodiments, the electrical leads 122, 127 comprise commercially available leads of a commercially available pacemaker of Medtronic Plc, Boston Scientific Corporation, Abbott Laboratories, or another suitable supplier.

FIG. 2A illustrates the cathode electrode 125 and the anode electrode 120 affixed to a central portion of the myocardial infarction region 110 of the myocardium 202. As illustrated, the cathode and anode electrodes 125, 120 are centrally located within the myocardial infarction region 110, disposed adjacent one, and separated by a distance 188. As further discussed below, in example operation, the two electrodes 120, 125 apply electricity selectively to the myocardial infarction region 110, with the electricity flowing between the electrodes 120, 125. Electrical signals thus propagate through the myocardial infarction region 110.

Turning now to FIG. 3, an example transvenous embodiment will be discussed as an alternative to the example epicardial embodiments that FIGS. 1 and 2 respectively illustrate as discussed above. FIG. 3 illustrates the system 150B in an example operating environment whereby a myocardial condition is treated.

In the example application of FIG. 3, the myocardial condition comprises a myocardial infarction region 110 of the heart 100 that the system 150B is configured to treat. As shown in the cross sectional view of the heart 100 that FIG. 3 illustrates, the example myocardial infarction region 110 extends from the epicardium 101 to the endocardium 222, and the myocardium 202 comprises the myocardial infarction region 110.

FIG. 3 illustrates the system 150B as applied in an example transvenous implantation. An example implantation procedure can comprise a medical practitioner making an incision in a suitable vein of a treated subject, such as a human patient. With aid of fluoroscopic imaging, the practitioner can pass the bipolar electrical lead 220 along the vein and into a chamber 209 of the heart 100, adjacent the myocardial infarction region 110. The medical practitioner can screw a fastener 119, which is distally disposed on the distal end 215 of the lead 220 as illustrated in FIG. 1B, through the endocardium 222 and into the myocardium 202. So screwed, the fastener 119 can affix or fasten the distal end 215 of the bipolar electrical lead 220 to a central portion of the myocardial infarction region 110. Once the distal end 215 is secured, the medical practitioner can connect the lead 220 to the instrument 175, for instance plugging the lead 220 into a receptacle (not illustrated) of the instrument 175. The medical practitioner can implant the instrument 175 below a clavicle in a chest of the subject, for example.

Turning now to FIGS. 4, 5, 6, and 7, some example embodiments of the instrument 175 that are compatible with the epicardial embodiments of FIGS. 1 and 2 and with the transvenous embodiment of FIG. 3 will be further discussed.

Figure 4:
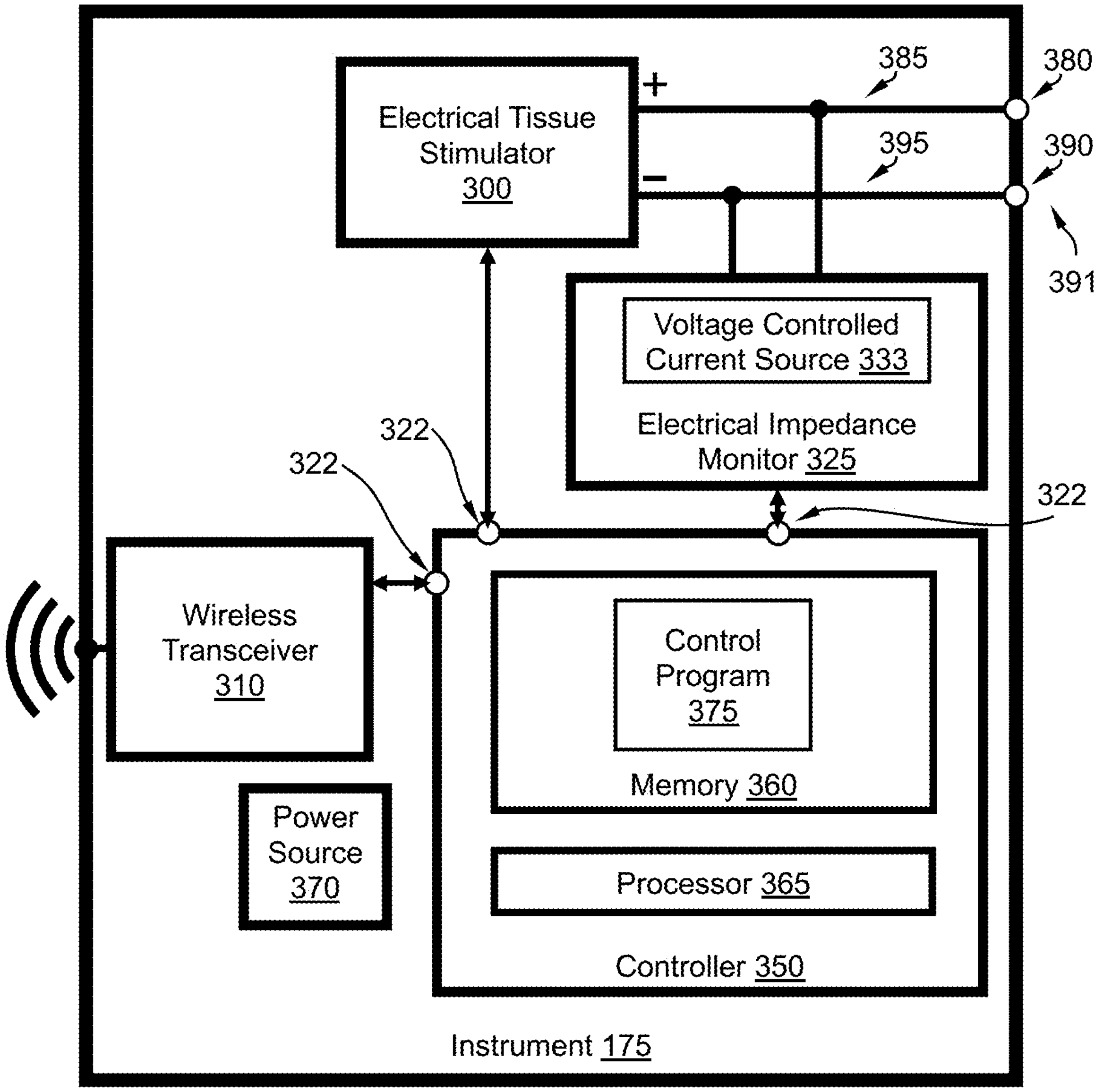
FIG. 4 is a functional block diagram of instrument of a system for treating a myocardial condition in accordance with some example embodiments of the disclosure.
Figure 5A:
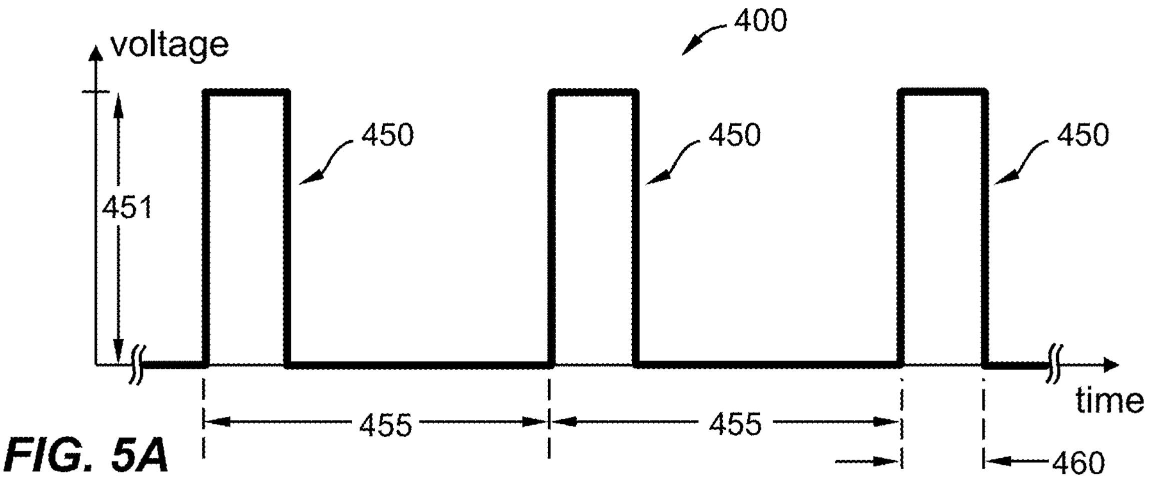
FIGS. 5A and 5B (collectively FIG. 5) are plots of electrical signals for stimulating favorable therapeutic change of a myocardium that comprises a myocardial condition in accordance with some example embodiments of the disclosure.
Figure 5B:
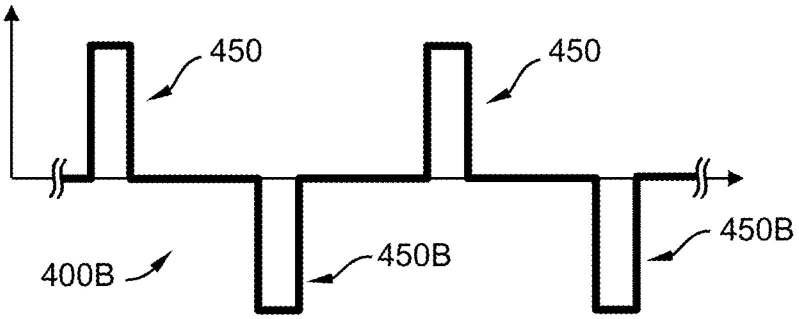
Figure 6:
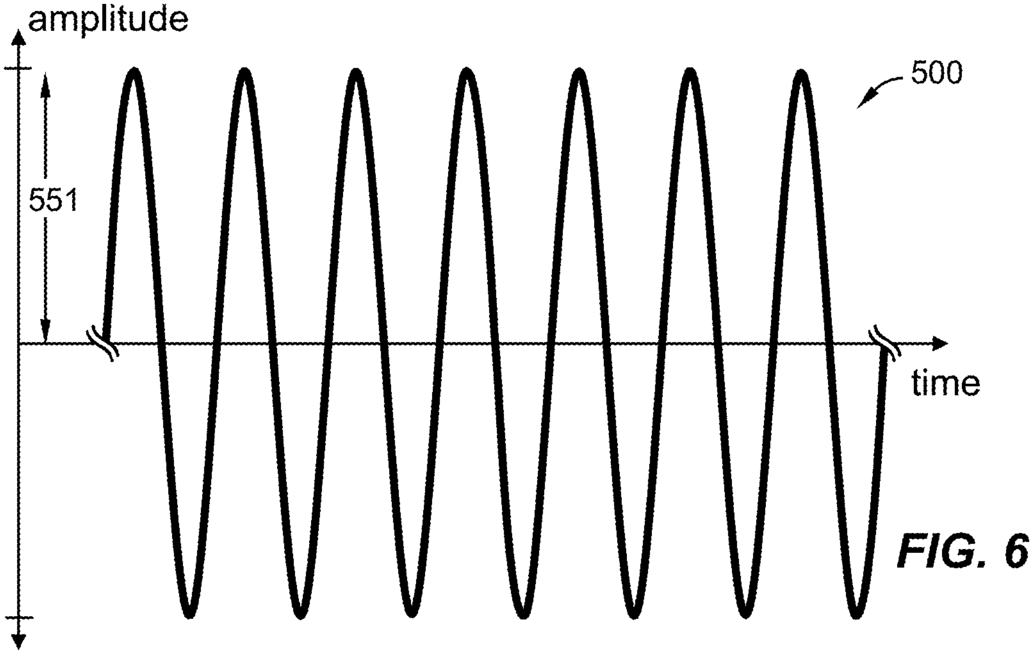
FIG. 6 is a plot of an electrical signal for monitoring therapeutic change and therapeutic state of a myocardium that comprises a myocardial condition in accordance with some example embodiments of the disclosure.
Figures 7A, 7B, 7C:
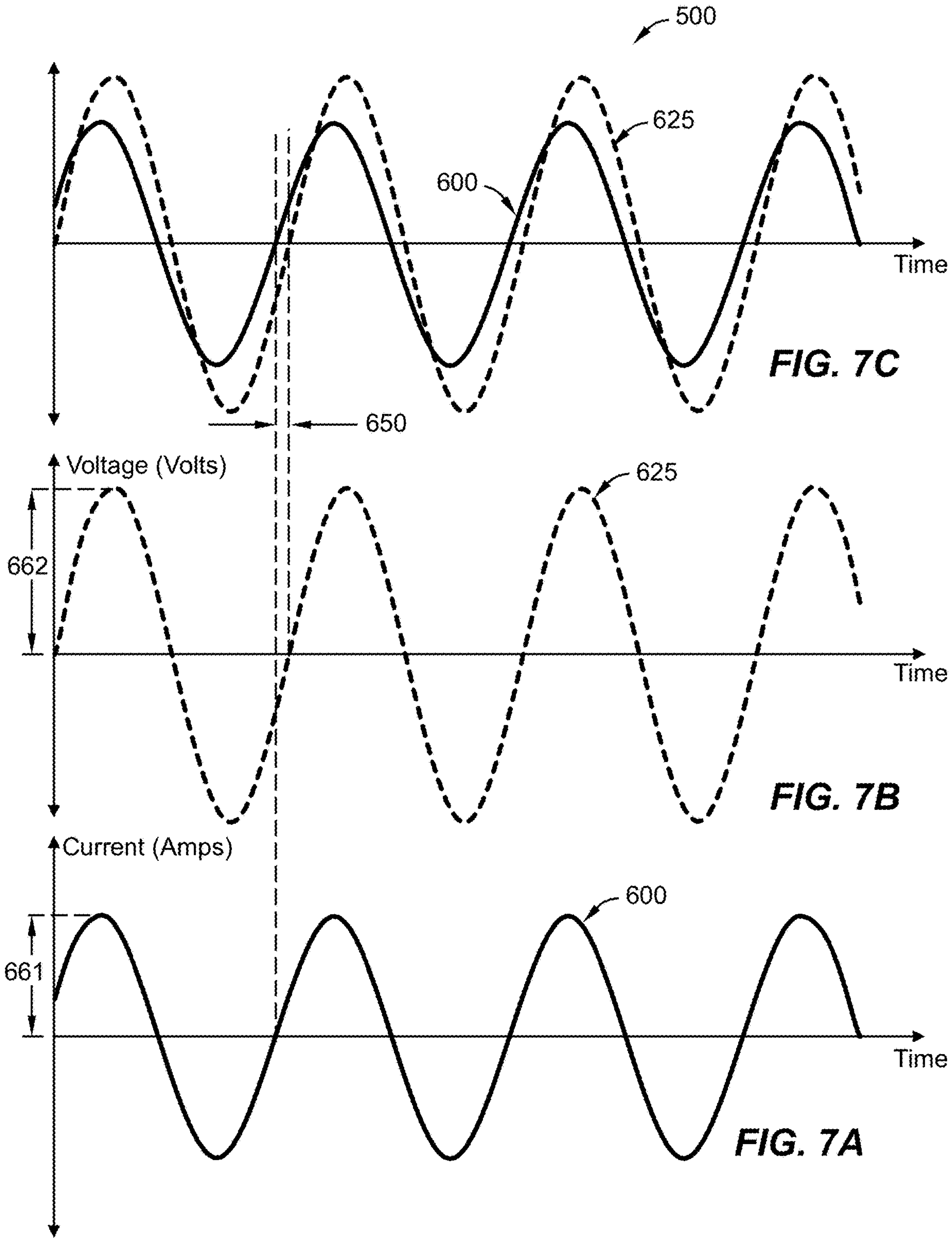
FIGS. 7A, 7B, and 7C (collectively FIG. 7) are current and voltage plots of an electrical signal for monitoring therapeutic change and therapeutic state of a myocardium that comprises a myocardial condition in accordance with some example embodiments of the disclosure.

FIG. 4 illustrates a representative functional block diagram of the example instrument 175 of the example system 150, 150A, 150B for treating a myocardial condition according to some embodiments of the disclosure. FIGS. 5A and 5B illustrate representative plots of example electrical signals 400, 400B for stimulating favorable therapeutic change of a myocardium 202 that comprises a myocardial condition according to some embodiments of the disclosure. FIG. 6 illustrates a representative plot of an example electrical signal 500 for monitoring therapeutic change and therapeutic state of a myocardium 202 that comprises a myocardial condition according to some embodiments of the disclosure. FIG. 7A, 7B, and 7C illustrate plots of representative current and voltage waveforms 600, 625 of an example electrical signal 500 for monitoring therapeutic change and therapeutic state of a myocardium 202 that comprises a myocardial condition according to some embodiments of the disclosure.

The below discussion of FIGS. 4, 5, 6, 7, and 8 makes nonlimiting reference to certain illustrated example embodiments. Those skilled in the art having benefit of this disclosure will appreciate that FIGS. 4, 5, 6, 7, and 8 (and the following discussion) apply to the example systems 150, 150A, 150B respectively illustrated by FIGS. 1, 2, and 3 as discussed above, and further apply to other systems.

After an overview of the functional block diagram of FIG. 4, the following discussion will take up individual functional blocks of the diagram. As FIG. 4 illustrates, the example instrument 175 comprises an electrical tissue stimulator 300, an electrical impedance monitor 325, a controller 350, a wireless transceiver 310, and a power source 370. The electrical tissue stimulator 300 generates stimulating electrical signals 400 that selectively stimulate the myocardial infarction region 110 and induce favorable therapeutic change in the region 110. The electrical impedance monitor 325 monitors the induced therapeutic change. The electrical impedance monitor 325 can determine or assess degree of therapeutic change according to change in electrical impedance of the region 110 that occurs over a course of treatment. A voltage controlled current source 333, which the electrical impedance monitor 325 comprises, generates electrical signals 500 for probing or interrogating the myocardial infarction region 110. The controller 350 supports embedded control of the system 150, including controlling the electrical tissue stimulator 300 and the electrical impedance monitor 325. The controller 350 comprises a processor 365 and memory 360. The memory 360 stores a control program 375 that executes on the processor 365. The wireless transceiver 310 supports outgoing data transmissions and incoming commands. The power source 370 provides power to the system 150, 150A, 150B including to the instrument 175 and circuitry thereof. For example, the power source 370 can comprise a battery electrically coupled to the electrical tissue stimulator 300, the electrical impedance monitor 325, the controller 350, and the wireless transceiver 310, each of which comprises circuitry.

Some example embodiments of the electrical tissue stimulator 300 will now be further discussed. Discussion of the electrical impedance monitor 325 follow. Then, discussion will turn to the controller 350.

The electrical tissue stimulator 300 comprises an example embodiment of a tissue stimulator and further comprises an example embodiment of a stimulator. An anode line 385 and a cathode line 395 extend from the electrical tissue stimulator 300, respectively to an anode port 380 and a cathode port 390. The anode port 380 and the cathode port 390 can comprise an output 391 of the instrument 175. In some example embodiments, the output 391 comprises a pair of connectors for connecting the instrument 175 to the unipolar cathode electrical lead 127 and the unipolar anode electrical lead 122 that FIG. 2 illustrates. In some example embodiments, the output 391 comprises a single connector for connecting the instrument 175 to the bipolar electrical lead 220 that FIGS. 1 and 3 illustrate. In some example embodiments, the medical practitioner can manually make the connections during implantation.

In some example embodiments, the electrical tissue stimulator 300 generates the electrical signal 400 that FIG. 5A illustrates in plot format. That is, the electrical tissue stimulator 300 can output electricity according to the waveform plotted by FIG. 5A. The electrical signal 400 can be viewed as a stimulating electrical signal 400 and may be referred to as the stimulating electrical signal 400 without limitation.

In some example embodiments, the stimulating electrical signal 400 is subthreshold with respect to evoking an electrical pacing response from the heart 100. The stimulating electrical signal 400 comprises an example embodiment of subthreshold electricity that can be applied to the myocardial infarction region 110. In some example embodiments, the stimulating electrical signal 400 comprises a pulse voltage 451 that is subthreshold with respect to evoking an electrical pacing response from the heart 100. In some example embodiments, the stimulating electrical signal 400 comprises electrical pulses 450 that are subthreshold with respect to evoking an electrical pacing response from the heart 100. Accordingly, the stimulating electrical signal 400 can avoid causing or evoking an electrical pacing response. The term "subthreshold," as used herein, generally refers to an electrical signal or stimulus that is inadequate to evoke an electrical pacing response in a subject's heart 100.

The example stimulating electrical signal 400 of FIG. 5A comprises an ongoing series of electrical pulses 450. As illustrated, each electrical pulse 450 comprises a pulse duration 460 and the pulse voltage 451, and the electrical pulses 450 have a cycle time 455.

In some example embodiments, the pulse duration 460 is 0.05 milliseconds, the pulse voltage 451 is 0.8 volts, and the electrical pulses 450 have a cycle time 455 of 0.25 seconds. In some example embodiments, the numerical values disclosed in the immediately preceding sentence can be nominal numerical values, approximate numerical values, or substantial numerical values. In some example embodiments, the system 150, 150A, 150B can be configured to operate with a pulse duration 460, a pulse voltage 451, and a cycle time 455 that are within 15 percent of those disclosed numerical values. With a cycle time 455 of 0.25 seconds, the electrical tissue stimulator 300 generates and outputs an electrical pulse 450 every 0.25 seconds or 4 electrical pulses 450 per second. As such, a nominal pulse frequency of the stimulating electrical signal 400 can be characterized as 4 hertz (Hz). The numerical values disclosed in this paragraph generally result in a stimulating electrical signal 400 that is subthreshold for an adult subject. The 0.8 volts of pulse voltage 451 drives or yields an electrical current through the myocardial infarction region 110. The magnitude of this electrical current can depend on the electrical characteristics of the myocardial infarction region 110.

In some example embodiments, the electrical tissue stimulator 300 comprises a voltage controlled current source that controls pulse voltage 451 to achieve a target pulse current, such as 2 milliamps of electrical current. In some example embodiments, the resulting pulse voltage 451 can be approximately 0.8 volts. The pulse duration 460 can be set to 0.05 milliseconds, and the cycle time 455 can be set to 0.25 seconds. The resulting stimulating electrical signal 400 can be subthreshold. In some example embodiments, the numerical values disclosed in this paragraph can be approximate or substantial numerical values.

In some example embodiments, the pulse voltage 451 can be set according to distance 188 or physical separation between the implanted anode electrode 120 and the implanted cathode electrode 125. (FIG. 2A illustrates an example embodiment of the distance 188.) In some example embodiments, a numerical value stored in the memory 360 of the controller 350 can set pulse voltage 451 of each electrical pulse 450. That is, the electrical tissue stimulator 300 can generate and output electrical pulses 450 having a voltage 451 defined by a configurable number stored in the memory 360. In some example embodiments, the medical practitioner specifies the pulse voltage 451 according to the distance 188 between the two implanted electrodes 120, 125. In some example embodiments, the pulse voltage 451 is set to 4 volts per centimeter of distance 188 between the cathode and anode electrodes 125, 120. In some example embodiments, at this voltage, each electrical pulse 450 can produce an electrical current of approximately 2 milliamps. With 0.5 centimeters of distance 188 separating the cathode and anode electrodes 125, 120, the pulse voltage 451 can be set to 2.0 volts. In some example embodiments, the medical practitioner specifies the pulse voltage 451 on a subject-specific basis according to medical judgment, and the specified pulse voltage 451 is entered into the memory 360. In some example embodiments, the numerical values disclosed in this paragraph can be approximate or substantial numerical values.

In some example embodiments, application of the stimulating electrical signal 400 is coordinated or synchronized with intrinsic electrical activity of the cardiac cycle of the heart 100. For example, in some embodiments, the pulses 450 of the stimulating electrical signal 400 transmit through the myocardial infarction region 110 during one or more portions of the cardiac cycle when intrinsic electrical activity of the heart 100 is relatively low.

In some example embodiments, the stimulating electrical signal 400 is subthreshold and the pulse duration 460 is in a range 0.01 milliseconds to 1 millisecond, the pulse cycle time 455 is in a range of 0.1 seconds to 2 seconds, and the pulse voltage 451 is in a range of 0.2 volts to 2 volts. In some example embodiments, the numerical values disclosed in this paragraph can be approximate or substantial numerical values. In some example embodiments, the ranges disclosed in this paragraph can be approximate or substantial ranges.

In some example embodiments, the stimulating electrical signal 400 is subthreshold and the pulse duration 460 is in a range 0.05 milliseconds to 0.5 millisecond, the pulse cycle time 455 is in a range of 0.2 seconds to 1 second, and the pulse voltage 451 is in a range of 0.5 volts to 1.5 volts. The numerical values disclosed in this paragraph can be approximate or substantial numerical values. Further, the ranges disclosed in this paragraph can be approximate or substantial ranges.

In some example embodiments, the stimulating electrical signal 400 is subthreshold and comprises a pulse voltage 451 that is not greater than 2.0 volts. In some example embodiments, the stimulating electrical signal 400 is subthreshold and comprises a pulse duration 460 that is not greater than 1.0 milliseconds. In some example embodiments, the stimulating electrical signal 400 is subthreshold and comprises a pulse cycle time 455 that is not more than 0.75 seconds. In some example embodiments, the numerical values disclosed in this paragraph can be approximate or substantial numerical values.

In some example embodiments, each electrical pulse 450 has a pulse voltage 451 selected to produce in the myocardial infarction region 110 a target electrical current density. In some example embodiments, that target electrical current density is in a range of 2 milliamps per centimeter to 20 milliamps per centimeter. These numerical values can be approximate or substantial numerical values. Further, the range can be an approximate or substantial range. In some example embodiments, each electrical pulse 450 has a pulse current selected to produce in the myocardial infarction region 110 a target electrical field strength.

FIG. 5B illustrates a plot of another stimulating electrical signal 400B that the electrical tissue stimulator 300 can generate and that the electrical leads 122, 127 can apply to the myocardial infarction region 110 in accordance with some example embodiments. In the example embodiment of FIG. 5B, the electrical pulses 450, 450B are of alternating polarity. That is, the stimulating electrical signal 400B comprises positive electrical pulses 400 interleaved with negative electrical pulses 450B.

In some example embodiments, the electrical tissue stimulator 300 is implemented in accordance with, uses, or practices the teachings of U.S. Pat. No. 8,489,186, issued Jul. 16, 2013 in the name of Rupak Mukherjee and Francis Spinale and entitled "Devices and Methods for Treatment of Myocardial Conditions," the entire disclosure of which is hereby incorporated herein by reference. Thus, the entire disclosure of said U.S. Pat. No. 8,489,186 is hereby incorporated herein by reference.

In some example embodiments, the electrical tissue stimulator 300 is implemented in accordance with, uses, or practices the teachings of the article authored by Mukherjee R, Rivers WT, Ruddy JM, Matthews RG, Koval CN, Plyler RA, Chang EI, Patel RK, Kern CB, Stroud RE, and Spinale FG, entitled "Long-Term Localized High-Frequency Electric Stimulation Within the Myocardial Infarct: Effects on Matrix Metalloproteinases and Regional Remodeling," published in *Circulation* with a date of 2010 Jul. 6, Volume 122, Issue 1, on pages 20-32 (doi: 10.1161/CIRCULATIONAHA.110.936872, Epub 2010 Jun. 21. PMID: 20566951, PMCID: PMC2946370), the entire disclosure of which is hereby incorporated herein by reference. Thus, the entire disclosure of said article entitled "Long-Term Localized High-Frequency Electric Stimulation Within the Myocardial Infarct: Effects on Matrix Metalloproteinases and Regional Remodeling" is hereby incorporated herein by reference.

In some example embodiments, the electrical tissue stimulator 300 is implemented in accordance with, uses, or practices the teachings of the article authored by Genau MC, Perreault PE, Romito E, Doviak H, Logdon CB, Ruble S, and Spinale FG, entitled "Institution of Localized High-Frequency Electrical Stimulation Targeting Early Myocardial Infarction: Effects on Left Ventricle Function and Geometry," published in *The Journal of Thoracic and Cardiovascular Surgery* with a date of 2018 August, Volume 156, Number 2, on pages 568-575 (doi: 10.1016/j.jtcvs.2018.01.104, Epub 2018 Mar. 12. PMID: 29609885), the entire disclosure of which is hereby incorporated herein by reference. Thus, the entire disclosure of said article entitled "Institution of Localized High-Frequency Electrical Stimulation Targeting Early Myocardial Infarction: Effects on Left Ventricle Function and Geometry" is hereby incorporated herein by reference.

In some example embodiments, the electrical tissue stimulator 300 is implemented via programming modification of a commercially available pacemaker, such as a commercially available pacemaker of Medtronic Plc, Boston Scientific Corporation, Abbott Laboratories, or another suitable supplier. In some example embodiments, the electrical tissue stimulator 300 comprises the commercially available pacemaker that has been reprogrammed to generate the stimulating electrical signal 400, with subthreshold signal amplitude, as discussed above. In some example embodiments, the electrical tissue stimulator 300 comprises a pulse generator of the commercially available pacemaker in which the pulse generator has been reconfigured to generate the stimulating electrical signal 400, with subthreshold signal amplitude, as discussed above. In some example embodiments, reconfiguring the pulse generator can comprise reprogramming. In some example embodiments, reconfiguring the pulse generator can comprise attenuating an output of the pulse generator. In some example embodiments, attenuating the output of the pulse generator can comprise applying a load in series with the output, whereby the load drops voltage. In some example embodiments, attenuating the output of the pulse generator can comprise applying a shunt to the output, wherein the shut diverts a portion of the pulse generator's output to a load.

Some example embodiments of the electrical impedance monitor 325 will now be further discussed. The example electrical impedance monitor 325 processes the electrical signal 500 that FIG. 6 illustrates to monitor electrical impedance of the myocardial infarction region 110 as the region 110 undergoes therapeutic change resulting from application of the stimulating electrical signal 400. Thus, the electrical impedance monitor 325 can monitor therapeutic response of the myocardial infarction region 110.

In some example embodiments, the electrical signal 500 can be viewed as a monitoring electrical signal 500 and may be referred to as the monitoring electrical signal 500 without limitation. As illustrated, the electrical signal 500 comprises an example embodiment of a sinusoidal electrical signal. The electrical impedance monitor 325 comprises an example embodiment of a therapeutic change monitor and further comprises an example embodiment of a tissue impedance monitor.

In the illustrated example of FIG. 4, the electrical impedance monitor 325 comprises a voltage controlled current source 333. The voltage controlled current source 333 comprises an example embodiment of a signal generator that is dedicated or substantially dedicated to producing the monitoring electrical signal 500.

Some other example embodiments differ from FIG. 4. In some such embodiments, the instrument 175 comprises one signal generator that generates the stimulating electrical signal 400 and the monitoring electrical signal 500. For example, the electrical tissue stimulator 300 can comprise a single signal generator that generates the stimulating electrical signal 400 and the monitoring electrical signal 500. The electrical tissue stimulator 300 can comprise such a signal generator in the form of a pulse generator of a commercially available pacemaker of Medtronic Plc, Boston Scientific Corporation, Abbott Laboratories, or another suitable supplier, with the pulse generator producing the stimulating electrical signal 400 and the monitoring electrical signal 500.

In the example form illustrated by FIG. 6, the monitoring electrical signal 500 comprises a sinusoidal waveform with a peak amplitude 551 and a frequency, which can be characterized in hertz or cycles per second. In the embodiment of FIG. 6, the monitoring electrical signal 500 has substantially one frequency. In some other embodiments, the monitoring electrical signal 500 can be composed of two or more discrete frequencies or a band of frequencies.

In some example embodiments, the monitoring electrical signal 500 can have: a specified voltage and a current that varies according to therapeutic change of the myocardial infarction region 110 caused by the stimulating electrical signal 400 ("a specified-voltage embodiment"); or a specified current and a voltage that varies according to therapeutic change of the myocardial infarction region 110 caused by the stimulating electrical signal 400 ("a specified-current embodiment"). The paragraph that follows immediately below discusses some example specified-voltage embodiments with reference to FIG. 6. Then, some example specified-current embodiments will be discussed with reference to FIG. 7.

In some examples of the specified-voltage embodiment, the monitoring electrical signal 500 has a voltage that has been specified or set. That is, the peak amplitude 551 represents a predetermined voltage. In operation, the electrical impedance monitor 325 generates a sinusoidally varying voltage (peaking as specified) that the anode and cathode electrodes 120, 125 apply to the myocardial infarction region 110. The sinusoidally varying voltage produces a complementary sinusoidally varying current that flows through the myocardial infarction region 110. The amplitude and timing of the sinusoidally varying current relative to the sinusoidally varying voltage correlates with electrical impedance of the myocardial infarction region 110. The electrical impedance monitor 325 can use this correlation to determine or assess electrical impedance of the myocardial infarction region 110 (via comparing the sinusoidally varying voltage to the sinusoidally varying current). Since therapeutic change of the myocardial infarction region 110 correlates with electrical impedance of the region 110, the instrument 175 can determine or assess therapeutic change based on change in electrical impedance of the region 110.

Some examples of the specified-current embodiment will now be discussed with reference to FIG. 7. In these examples, the monitoring electrical signal 500 can have a specified current 661 and a voltage 662 that changes according to therapeutic change of the myocardial infarction region 110 caused by the stimulating electrical signal 400. Thus, magnitude of the voltage 662 can correlate with, and thus indicate, therapeutic state; further, change in the voltage 662 can indicate therapeutic change.

FIG. 7A illustrates a representative current waveform 600 of the monitoring electrical signal 500. The current waveform 600 oscillates sinusoidally with a peak current 661 and a frequency. The peak current 661 can be specified or predetermined. The current waveform 600 represents an example embodiment of an oscillating current and further represents an example embodiment of a sinusoidal current.

FIG. 7B illustrates a representative voltage waveform 625 of the monitoring electrical signal 500 that has a peak voltage 662. The voltage waveform 625 coexists with the current waveform 600 of FIG. 7A. More specifically, an example embodiment of the monitoring electrical signal 500 has a sinusoidally varying voltage and a sinusoidally varying current, with FIG. 7A illustrating the sinusoidally varying current waveform 600 and FIG. 7B illustrating the sinusoidally varying voltage waveform 625. In other words, FIGS. 7A and 7B respectively illustrate current (in units of amps) and voltage (in units of volts) of the monitoring electrical signal 500 as the current and voltage oscillate sinusoidally over time at a common frequency. The voltage waveform 625 represents an example embodiment of an oscillating voltage and further represents an example embodiment of a sinusoidal voltage.

FIG. 7C illustrates the current and voltage waveforms 600, 625 overlaid. FIG. 7C further illustrates phase shift 650 between the current and voltage waveforms 600, 625.

As discussed above, electrical impedance of the myocardial infarction region 110 provides an indicator of therapeutic state of the region 110. And, change in electrical impedance of the region 110 indicates degree of favorable therapeutic change that has been achieved by application of the stimulating electrical signal 400.

Electrical impedance generally has two components, resistance and phase shift 650, each of which may vary with frequency. For a given frequency, the resistance component can be expressed as V equals I multiplied by R, where "V" represents peak voltage 662 expressed in volts, "I" represents peak current 661 expressed in amps, and "R" represents resistance expressed in ohms. For a given frequency, the phase-shift component of electrical impedance reflects the degree to which the voltage waveform 625 is shifted in time relative to the current waveform 600. (See phase shift 650 illustrated in FIG. 7C). The phase shift 650 can be viewed as a measure of lead or lag between the voltage and current waveforms 625, 600 of the monitoring electrical signal 500.

At 1 kilohertz, the resistive component of electrical impedance of the myocardial infarction region 110 correlates with therapeutic change. The correlation is sufficiently strong to use resistance of the myocardial infarction region 110 at 1 kilohertz as an indicator of therapeutic change of the region 110. As further discussed below, the voltage controlled current source 333 of the electrical impedance monitor 325 can generate the monitoring electrical signal 500 in a manner that facilitates and determining resistance.

Stepping briefly aside from the figures, as will be appreciated by those of ordinary skill in the art, a voltage controlled current source comprises an electrical circuit that can apply a specified current to a load and maintain the specified current while electrical resistance of the load changes. A voltage controlled current source maintains the specified current by adjusting voltage to compensate for the change in electrical resistance. If a voltage controlled current source is connected to a load having relatively low electrical resistance, it can use relatively low voltage to deliver the specified current. And if a voltage controlled current source is connected to a load having relatively high electrical resistance, it can use relatively high voltage to deliver the specified current. Accordingly, a voltage controlled current source can change voltage to maintain a specified level of current across varied loads or varied resistances.

Stepping now back to the figures, as further discussed below, the output voltage 662 of the illustrated voltage controlled current source 333 correlates with electrical impedance of the myocardial infarction region 110, which correlates with therapeutic state. Further, voltage change correlates with electrical impedance change, which correlates with therapeutic change. Voltage 662 thus indicates therapeutic state, and voltage change indicates therapeutic change.

The voltage controlled current source 333 effectively operates in compliance with the equality that voltage 662 equals current 661 multiplied by resistance. With the current 661 fixed to a specified value, the voltage controlled current source 333 maintains the equality by changing voltage 662 as resistance changes. Accordingly, with current 661 fixed, voltage 662 produced by the voltage controlled current source 333 correlates with resistance of the myocardial infarction region 110. Voltage 662 thus correlates with electrical impedance of the region 110. And since electrical impedance correlates with therapeutic state, voltage 662 correlates with therapeutic state of the region 110. It follows that change in voltage 662 correlates with therapeutic change of the region 110.

An example frequency of the monitoring electrical signal 500 is 1 kilohertz. (As discussed above, at 1 kilohertz, the resistive component of electrical impedance correlates sufficiently with therapeutic state.) Further, the peak current 661 can be set to a subthreshold level, such as 1 milliamp. As such, the illustrated current waveform 600 of the monitoring electrical signal 500 has a frequency of 1 kilohertz and a peak current 661 of 1 milliamp, while FIG. 7B illustrates the voltage waveform 625 of the monitoring electrical signal 500.

In application, the monitoring electrical signal 500 transmits over the single bipolar electrical lead 220 (or the pair of unipolar electrical leads 122, 127) and through the myocardial infarction region 110. The peak current 661 of the monitoring electrical signal 500 remains substantially at 1 milliamp while the myocardial infarction region 110 undergoes favorable therapeutic change (due to application of the stimulating electrical signal 400 as discussed above). As the myocardial infarction region 110 favorably responds to treatment, electrical impedance of the region 110 decreases. The voltage controlled current source 333 changes peak voltage 662 of the voltage waveform 625 to maintain 1 milliamp of peak current 661 as electrical impedance changes. The degree of voltage change indicates the degree of electrical impedance change, which indicates the degree of therapeutic change.

Accordingly, the peak voltage 662 that the voltage controlled current source 333 generates for the monitoring electrical signal 500 indicates therapeutic state of the myocardial infarction region 110, and the change in that voltage 662 over time indicates therapeutic change over time. Said another way, the peak voltage 662 of the monitoring electrical signal 500 indicates therapeutic state of the myocardial infarction region 110, and the change in that voltage 662 over time indicates therapeutic change over time.

The electrical impedance monitor 325 can thus process the electrical signal 500 to monitor electrical impedance, electrical impedance change, therapeutic state, and therapeutic change of the myocardial infarction region 110 over an extended course of therapy that comprises application of stimulating electrical signals 400.

In some example embodiments, the electrical impedance monitor 325 applies the monitoring electrical signal 500 to the myocardial infarction region 110 throughout the cardiac cycle of the heart to average out variation in electrical impedance attributable to the cardiac cycle.

In some example embodiments, the electrical impedance monitor 325 applies the monitoring electrical signal 500 to the myocardial infarction region 110 throughout the cardiac cycle of the heart and determines change in electrical impedance of the region 110 between systole and diastole. The electrical impedance monitor 325 can thus monitor the systole-diastole electrical impedance change over extended therapy as an indicator of therapeutic change.

In some example embodiments, the monitoring electrical signal 500 coordinates or synchronizes electrical impedance monitoring with intrinsic electrical activity of the cardiac cycle of the heart 100.

In some example embodiments, the monitoring electrical signal 500 has a duration of no less than 0.1 seconds. In some example embodiments, the monitoring electrical signal 500 has a duration in a range of 0.05 seconds to 5 seconds. The numerical values disclosed in this paragraph can be approximate or substantial numerical values. Further, the ranges disclosed in this paragraph can be approximate or substantial ranges.

In some example embodiments, the electrical impedance monitor 325 accounts for volume of the myocardial infarction region 110 through which the monitoring electrical signal 500 propagates. By accounting for volume, the electrical impedance monitor 325 can translate resistance between the two electrodes 120, 125 to resistivity of the myocardial material that makes up the myocardial infarction region 110.

In some example embodiments, the monitoring electrical signal 500 is subthreshold and has a frequency in a range of 0.5 kilohertz to 1,000 kilohertz and a peak current 661 in a range of 0.1 milliamps to 15 milliamps. The numerical values disclosed in this paragraph can be approximate or substantial numerical values. Further, the ranges disclosed in this paragraph can be approximate or substantial ranges.

In some example embodiments, the monitoring electrical signal 500 is subthreshold and comprises a frequency of 1 kilohertz, 41 kilohertz, 307 kilohertz, or 1,000 kilohertz. These numerical values can be approximate or substantial numerical values.

In some example embodiments, the electrical impedance monitor 325 utilizes at least two discrete frequencies for monitoring electrical impedance, wherein the two discrete frequencies are separated by no less than approximately 39 kilohertz.

In some example embodiments, the electrical impedance monitor 325 utilizes phase shift 650 between the current waveform 600 and the voltage waveform 625 of the monitoring electrical signal 500 as an indicator of therapeutic state or therapeutic change. In some such embodiments, the monitoring electrical signal 500 is subthreshold and has a peak current 661 of approximately 1 milliamp and a frequency of approximately 41 kilohertz.

In some example embodiments, the electrical impedance monitor 325 is implemented in accordance with, uses, or practices the teachings of the article authored by Aranyó J, Martínez-Falguera D, Bazan V, Fadeuilhe E, Teis A, Sarrias A, Rodríguez-Leor O, Curiel C, Villuendas R, Bayés-Genís A, Gálvez-Montón C, and Bisbal F, entitled "Biophysical Tissue Characterization of Ventricular Tachycardia Substrate With Local Impedance Mapping to Predict Critical Sites," published in Journal of the American College of Cardiology: Clinical Electrophysiology with a date of 2023 June, Volume 9, Issue 6 on pages 765-775 (doi: 10.1016/j.jacep.2022.11.023, Epub 2023 Jan. 18. PMID: 36752472), the entire disclosure of which is hereby incorporated herein by reference. Thus, the entire disclosure of said article entitled "Biophysical Tissue Characterization of Ventricular Tachycardia Substrate with Local Impedance Mapping to Predict Critical Sites" is hereby incorporated herein by reference.

In some example embodiments, the electrical impedance monitor 325 is implemented in accordance with, uses, or practices the teachings of the article authored by Amorós-Figueras G, Jorge E, García-Sánchez T, Bragós R, Rosell-Ferrer J, and Cinca J, entitled "Recognition of Fibrotic Infarct Density by the Pattern of Local Systolic-Diastolic Myocardial Electrical Impedance," published in Frontiers in Physiology with a date of 2016 Aug. 31, Volume 7, Article 389 (doi: 10.3389/fphys.2016.00389. PMID: 27630580; PMCID: PMC5006502), the entire disclosure of which is hereby incorporated herein by reference. Thus, the entire disclosure of said article entitled "Recognition of Fibrotic Infarct Density by the Pattern of Local Systolic-Diastolic Myocardial Electrical Impedance" is hereby incorporated herein by reference.

Turning now to the controller 350, a discussion of some example embodiments follows. In the example functional block diagram of FIG. 4, the controller 350 of the instrument 175 is electrically coupled and operably coupled with the electrical tissue stimulator 300, the electrical impedance monitor 325, and the wireless transceiver 310. As illustrated, the controller 350 can communicate bidirectionally with and control each of the electrical tissue stimulator 300, the electrical impedance monitor 325, and the wireless transceiver 310.

In some example embodiments, the controller 350 comprises a microcontroller or a microcontroller unit (MCU) that comprises input/output interfaces 322 to the electrical tissue stimulator 300, the electrical impedance monitor 325, and the wireless transceiver 310. The electrical tissue stimulator 300, the electrical impedance monitor 325, and the wireless transceiver 310 can comprise peripherals. The input/output interfaces 322 provide the controller 350 a capability to receive information, in the form of binary data, from the electrical tissue stimulator 300, the electrical impedance monitor 325, and the wireless transceiver 310. The controller 350 can further send instructions or commands through the input/output interfaces 322 to the electrical tissue stimulator 300, the electrical impedance monitor 325, and the wireless transceiver 310. The electrical tissue stimulator 300, the electrical impedance monitor 325, and the wireless transceiver 310 can execute tasks responsive to receiving the instructions or commands, for example.

As illustrated, the example controller 350 comprises a processor 365 and memory 360. In some example embodiments, the processor 365, the memory 360, and the input/output interfaces 322 are on a single chip or in an integrated package or format. In some example embodiments, the processor 365 can comprise a central processing unit (CPU) or a microprocessor.

As illustrated by FIG. 4, a control program 375 is stored in the memory 360. For example, the memory 360 can comprise non-transitory memory or non-volatile memory that stores instructions of the control program 375. As further discussed below with reference to FIG. 8, some example embodiments of the control program 375 can define or set forth a process or method (or steps thereof) for treating a myocardial condition. The processor 365 can execute the control program 375.

Figure 8:
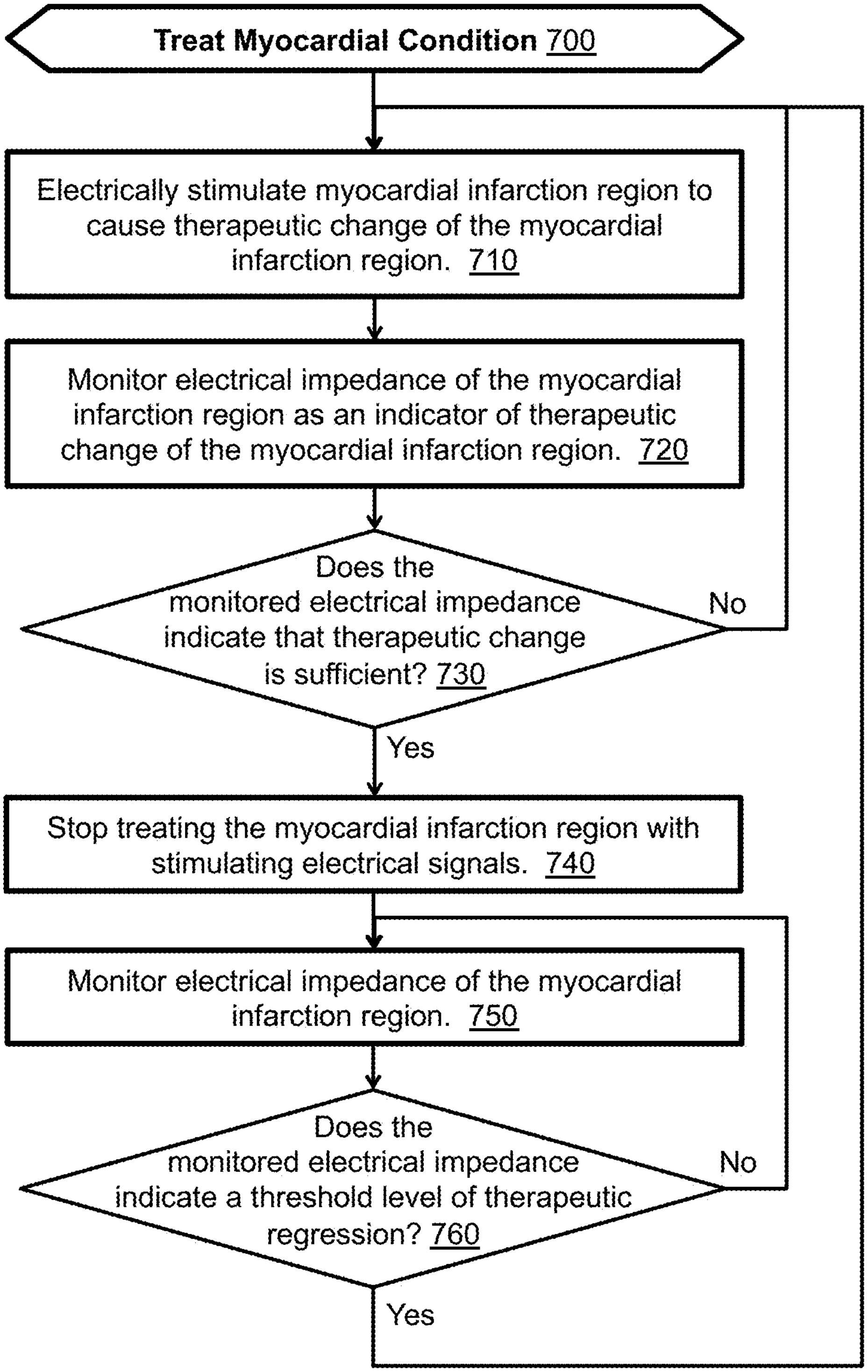
FIG. 8 is flowchart of a method or process for treating a myocardial condition in accordance with some example embodiments of the disclosure.

In some example embodiments, executing the control program 375 can comprise the controller 350 performing a process 700 in accordance with the flowchart of FIG. 8 and accompanying discussion. In some example embodiments, executing the control program 375 can comprise the instrument 127 performing a process 700 in accordance with the flowchart of FIG. 8 and accompanying discussion. In some example embodiments, executing the control program 375 can comprise the system 150, 150A, 150B performing a process 700 in accordance with the flowchart of FIG. 8 and accompanying discussion.

In some example embodiments, the process 700 can comprise treating a myocardial condition by iteratively: applying subthreshold electricity that is operative to cause therapeutic change; and monitoring the therapeutic change. In some example embodiments, the system 150, 150A, 150B is implantable and configured to practice this process 700 autonomously. In some example embodiments, this process 700 is autonomous.

In some example embodiments, the process 700 can comprise treating a myocardial condition by: an implantable system applying to a myocardium subthreshold electricity that is operative to cause therapeutic change under guidance of the implantable system monitoring the myocardium for the therapeutic change. In some example embodiments, the system 150, 150A, 150B is implantable and configured to practice this process 700 autonomously. In some example embodiments, this process 700 is autonomous.

Turning now to FIG. 8, this figure illustrates a representative flowchart of an example method or process 700 for treating a myocardial condition according to some embodiments of the disclosure. The flowchart of FIG. 8 further illustrates an example embodiment of the control program 375. The process 700 can comprise the processor 365 executing the control program 375. In accordance with some example embodiments of the process 700, the medical condition comprises a myocardial lesion or a myocardial infarction region and will be largely referred to below as the myocardial infarction region 110, without limitation.

At block 710 of the process 700, the system 150, 150A, 150B electrically stimulates the myocardial infarction region 110 to cause favorable therapeutic change of the region 110. The system 150, 150A, 150B has typically been implanted prior to execution of block 710. As discussed above, the electrical tissue stimulator 300 generates the stimulating electrical signal 400, one or more electrical leads 122, 127, 220 carry the signal 400 to the myocardial infarction region 110, and the signal 400 propagates through the region 110. The myocardial infarction region 110 undergoes favorable therapeutic change in response to stimulation by the signal 400. Stimulation can comprise administering, over multiple iterations of block 710, a therapeutically effective amount and form of electricity, electrical energy, or electrical signals as described herein. As discussed below, the execution of block 710 can proceed fully autonomously or with at least some human input.

In some example embodiments, block 710 continues executing for a predefined amount of time. When that time expires, electrical stimulation of the myocardial infarction region 110 stops, and process 700 executes block 720. For example, the controller 350 can measure or clock time and, upon expiration of the predefined period of time, issue a stop command to the electrical tissue stimulator 300. That is, the controller 350 can deactivate the electrical tissue stimulator 300. In some example embodiments, the predefined period of time is not more than 24 hours or not more than approximately 24 hours. In some example embodiments, the predefined period of time is one week or approximately one week. In some example embodiments, the predefined period of time is in a range of approximately one week to six weeks.

As an alternative to running autonomously on a timer, in some example embodiments, the electrical tissue stimulator 300 continues electrical stimulation of the myocardial infarction region 110 until the wireless transceiver 310 receives a command to stop the electrical stimulation. For example, the subject (who is a human patient in this case) may go to the medical practitioner's office for a checkup on a timetable set by the practitioner, such as on a monthly or semiannual basis following implantation. During the checkup, the medical practitioner can establish a wireless communication link with the instrument 175 through the wireless transceiver 310. The medical practitioner can issue the command via a radio (not illustrated) that operates on the industrial, scientific, and medical (ISM) band of the radio frequency spectrum. The wireless transceiver 310 can receive the command and forward the command to the controller 350. Responsive to receipt of the command from the wireless transceiver 310, the controller 350 can command the electrical tissue stimulator 300 to stop electrically stimulating the myocardial infarction region 110. Thus, the controller 350 can deactivate the electrical tissue stimulator 300 according to the medical practitioner's medical judgment.

Process 700 proceeds to block 720 from block 710. At block 720, the electrical impedance monitor 325 monitors electrical impedance of the myocardial infarction region 110 as an indicator of therapeutic state or therapeutic change of the region 110 attributable to application of subthreshold electricity at block 710. As discussed above, monitoring electrical impedance can comprise electrically probing the myocardial infarction region 110 by applying to the region 110 the monitoring electrical signal 500 of known current and processing the signal, for example by measuring voltage 662 of the signal 500.

Once the electrical impedance monitor 325 acquires electrical impedance information from the region 110, process 700 executes decision block 730. As further discussed below, decision block 730 makes a determination as to whether a monitoring result of block 720 satisfies a criterion and directs taking one of two actions according to the determination. In the example flowchart of FIG. 8, a first of the two actions comprises electrically stimulating the myocardial infarction region 110 and monitoring the region 110 for electrical impedance or change in electrical impedance. The second of the two actions comprises monitoring for therapeutic regression.

As flowcharted by FIG. 8, the decision of decision block 730 regards whether the monitored electrical impedance indicates that sufficient therapeutic change has occurred. Thus at block 730, a decision is made as to whether therapeutic change has favorably advanced to a degree that warrants stopping the application of stimulating electrical signals 400 to the myocardial infarction region 110.

In some example embodiments, block 730 makes the decision based on electrical impedance information from a single impedance-monitoring session that occurs at block 720. In some other example embodiments, the decision of block 730 uses information from multiple impedance-monitoring sessions. For example, process 700 may iterate blocks 710 and 720 a predetermined number of times before executing decision block 730.

Discussion of three categories of example embodiments of decision block 730 follows.

In some example embodiments of the first category, the decision of block 730 comprises human input. For example, the instrument 175 can transmit impedance-monitoring results to the medical practitioner via the wireless transceiver 310. The medical practitioner can review the impedance-monitoring results and decide whether to stop or continue treatment.

If the medical practitioner decides to stop treatment, then the practitioner sends a wireless stop command that the controller 350 receives by way of the wireless transceiver 310. Responsive to receiving the stop command, execution of process 700 proceeds from block 730 to block 740. If, the medical practitioner sends a continue command, then execution of process 700 loops from block 730 back to block 710 and electrical stimulation resumes.

In some example embodiments of the second category, the controller 350 autonomously makes the decision of block 730 according to a criterion or according to criteria. For example, the controller 350 can make the decision by comparing the monitored electrical impedance to a threshold electrical impedance value that is stored in the memory 360. If the monitored electrical impedance meets the threshold, then the controller 350 can decide that the degree of therapeutic change suffices.

The threshold can be established according to electrical impedance of normal versus infarcted myocardial tissue. Electrical impedance of normal myocardial tissue is generally in a range of 10-20 ohms, while electrical impedance of infarcted myocardial tissue is generally five times the normal electrical impedance. The medical practitioner can use the system 150, 150A, 150B to test electrical impedance of infarcted and normal tissue of the subject's heart 100 during the implantation procedure of the system 150, 150A, 150B. The test results can provide subject-specific electrical impedance data. In some example embodiments, the medical practitioner determines the threshold based on the foregoing norms of normal-vs-infarcted electrical impedance, the results of the subject-specific electrical impedance tests, and medical judgment.

For example, the practitioner's tests on the subject's heart 100 could measure 75 ohms of electrical impedance in the myocardial infarction region 110 and 15 ohms of electrical impedance in normal myocardial tissue. In this case, the medical practitioner might decide that 30 ohms is an appropriate threshold for the decision of block 730 and enter that numerical value into the instrument 175 during the implantation procedure.

When process 700 executes decision block 730, the controller 350 compares the electrical impedance results (from block 720) to the threshold value of 30 ohms that the practitioner entered. If the electrical impedance monitor 325 has found that the electrical impedance of the myocardial infarction region 110 is 30 ohms or less, then the decision block 703 makes a positive determination and process 700 executes block 740. If, on the other hand, electrical impedance remains above 30 ohms, then execution of process 700 loops back to block 710 and electrical stimulation of the myocardial infarction region 110 resumes. Thus, process 700 iterates blocks 710, 720, and 730 until the controller 350 makes a determination at block 730 that a sufficient degree of favorable therapeutic change has been achieved.

In some example embodiments of the third category, the controller 350 autonomously makes the decision of block 730 based on change in electrical impedance over time or an electrical impedance trend. The controller 350 stores in the memory 360 a history of readings of electrical impedance of the myocardial infarction region 110. That is, the controller 350 records electrical impedance readings taken at successive executions of block 720. This historical data can include an initial electrical impedance reading taken during implantation or shortly after implantation is complete.

The decision of block 730 can comprise using the historical data to determine whether electrical impedance has fallen a predetermined amount. The controller 350 can implement the decision by comparing the most recent electrical impedance reading to the initial electrical impedance reading. For example, if the most recent electrical impedance reading is greater than a threshold percentage of the initial electrical impedance reading, electrical stimulation can continue (via looping from decision block 730 back to decision block 710). With the threshold percentage set to the example value of 50 percent, process 700 continues iterating blocks 710, 720, and 730 until electrical impedance of the myocardial infarction region 110 falls to at least 50 percent of the region's initial electrical impedance. A 50 percent drop in electrical impedance can generally correlate with favorably reducing myocardial expansion by approximately 50 percent.

Once the controller 350 determines that a sufficient degree of favorable therapeutic has been achieved, block 740 executes. At block 740, the controller 350 stops the treatment of electrically stimulating the myocardial infarction region 110. Process 700 can either end with execution of block 740 or continue according to the flowchart of FIG. 8.

As illustrated by FIG. 8, process 700 proceeds from block 740 to block 750. At block 750, the electrical impedance monitor 325 monitors electrical impedance of the myocardial infarction region 110 as an indicator of therapeutic change. As discussed above with reference to block 720, monitoring of the myocardial infarction region 110 can comprise probing or interrogating the region 110 with the monitoring electrical signal 500 and measuring or observing electrical impedance of the region 110.

Process 700 proceeds from block 750 to decision block 760. As discussed above with reference to decision block 730, decision block 760 can execute according to a schedule, periodically, or upon the instrument 175 receiving a wirelessly prompt or other command issued by the medical practitioner.

As further discussed below, decision block 760 makes a determination as to whether a monitoring result of block 750 satisfies a criterion and directs taking one of two actions according to the determination. In the example flowchart of FIG. 8, a first of the two actions comprises resuming electrical stimulation of the myocardial infarction region 110 and monitoring the region 110 for electrical impedance or change in electrical impedance. The second of the two actions comprises monitoring the myocardial infarction region 110 for therapeutic regression without resuming electrical stimulation of the region 110.

At decision block 760, the controller 350 determines whether the myocardial infarction region 110 has unfavorably changed or regressed to a degree that warrants resuming the application of stimulating electrical signals 400. In some example embodiments, the controller 350 makes the decision of block 760 according to a criterion or according to criteria. For example, making the decision can start with retrieving from the memory 360 the favorable electrical impedance reading (or readings) that was the basis for the "yes" decision at block 730, which resulted in execution of block 740 as discussed above. The controller 350 can compare that decisive electrical impedance reading with the most recent electrical impedance reading acquired at block 750. If the comparison shows a threshold degree of increase in electrical impedance, then process 700 loops back to block 710, and electrical stimulation of the myocardial infarction region 110 resumes. If not, process 700 iterates block 750 and 760 to continue monitoring the myocardial infarction region 110 for a degree of therapeutic regression that warrants resuming electrical stimulation of the region 110.

In some example embodiments, 25 percent is the threshold degree of increase in electrical impedance for triggering resuming electrical stimulation. Monitoring of the myocardial infarction region 110 thus continues until the electrical impedance monitor 325 measures at least a 25-percent increase in electrical impedance. When an increase in electrical impedance of at least 25 percent occurs, application of the stimulating electrical signals 400 resumes.

In some example embodiments, the controller 350 autonomously makes the decision of block 760. In some other example embodiments, the instrument 175 wirelessly transmits electrical impedance readings to the medical practitioner who makes the decision. The practitioner can review the electrical impedance readings and decide whether to command the instrument 175 to continue monitoring electrical impedance of the myocardial infarction region 110 or to resume electrical stimulation of the region 110.

Useful technology for treating myocardial conditions has been described. From the description, it will be appreciated that an embodiment of the disclosure overcomes limitations of the prior art. Those skilled in the art will appreciate that the technology is not limited to any specifically discussed application or implementation and that the embodiments described herein are illustrative and not restrictive. Furthermore, the particular features, structures, or characteristics that are set forth may be combined in any suitable manner in one or more embodiments based on this disclosure and ordinary skill. Those of ordinary skill having benefit of this disclosure can make, use, and practice a range of embodiments via combining the disclosed features and elements in permutations without undue experimentation and further by combining the disclosed features and elements with what is well known in the art. This disclosure not only includes the illustrated and described embodiments, but also provides a roadmap for additional embodiments using the various disclosed technologies, elements, features, their equivalents, and what is well known in the art. From the description of the example embodiments, equivalents of the elements shown herein will suggest themselves to those skilled in the art, and ways of constructing other embodiments will appear to practitioners of the art. Therefore, the scope of the technology is to be limited only by the appended claims.

What is claimed is:

1. An implantable device for treating a myocardial infarction region of a myocardium, the implantable device comprising:

an implantable housing comprising at least one electrical port;

at least one electrical lead comprising at least one distal end that is fastenable to said myocardial infarction region; and at least two distal electrodes that comprise a cathode electrode and an anode electrode, wherein the at least one electrical lead is electrically coupled to the at least one electrical port and is sized to extend from the at least one electrical port to the myocardial infarction region;

an electrical tissue stimulator disposed in the implantable housing and electrically coupled to the at least one electrical port, wherein the electrical tissue stimulator is configured to produce stimulating electrical signals for transmission over the at least one electrical lead and propagation through the myocardial infarction region for thickening or arresting thinning of the myocardial infarction region, and wherein the stimulating electrical signals are subthreshold; and an electrical impedance monitor disposed in the implantable housing and electrically coupled to the at least one electrical port, wherein the electrical impedance monitor is configured to produce monitoring electrical signals for transmission over the at least one electrical lead and probing the myocardial infarction region to monitor electrical impedance of the myocardial infarction region as an indication of degree of said thickening or arresting thinning of the myocardial infarction region attributable to said propagation of the stimulating electrical signals through the myocardial infraction region, and wherein the monitoring electrical signals are subthreshold and comprise:

a frequency in a range of 0.5 kilohertz to 1,000 kilohertz;

a peak current in a range of 0.1 milliamps to 15 milliamps; and a peak voltage correlating with the electrical impedance of the myocardial infarction region.

2. The implantable device of claim 1, wherein the electrical impedance monitor comprises a voltage controlled current source that is configured to produce the monitoring electrical signals.

3. The implantable device of claim 1, wherein the electrical impedance monitor comprises a voltage controlled current source that produces the monitoring electrical signals, wherein the monitoring electrical signals comprise a voltage and a current, and wherein the voltage controlled current source adjusts the voltage of the monitoring electrical signals to maintain the current of the monitoring electrical signals at a specified level while electrical impedance of the myocardial infarction region decreases due to thickening of the myocardial infarction region or increases due to thinning of the myocardial infarction region.

4. The implantable device of claim 3, wherein the electrical impedance monitor determines electrical impedance of the myocardial infarction region based on the voltage of the monitoring electrical signals as adjusted by the voltage controlled current source.

5. The implantable device of claim 3, wherein the electrical impedance monitor determines change in electrical impedance of the myocardial infarction region based on change in the voltage of monitoring electrical signals made by the voltage controlled current source.

6. The implantable device of claim 1, wherein the monitoring electrical signals comprise a specified current and a voltage that varies according to the degree of said thickening or arresting thinning of the myocardial infarction region attributable to said propagation of the stimulating electrical signals through the myocardial infraction region.

7. The implantable device of claim 1, wherein the monitoring electrical signals comprise a specified voltage and a current that varies according to the degree of said thickening or arresting thinning of the myocardial infarction region attributable to said propagation of the stimulating electrical signals through the myocardial infraction region.

8. The implantable device of claim 1, wherein the monitoring electrical signals comprise an oscillating current and an oscillating voltage, wherein the oscillating current comprises the peak current, wherein the oscillating voltage comprises the peak voltage, and wherein the electrical impedance monitor assesses electrical impedance of the myocardial infarction region based on the peak current and the peak voltage.

9. The implantable device of claim 1, wherein the electrical impedance monitor is configured to account for volume of the myocardial infarction region through which the monitoring electrical signals propagate.

10. The implantable device of claim 1, further comprising a controller disposed in the implantable housing, wherein the controller comprises:

a first input/output interface electrically coupled to the electrical impedance monitor;

a second input/output interface electrically coupled to the electrical tissue stimulator; and non-transitory memory and instructions stored thereon, that when executed by the controller, perform a method, wherein the method comprises:

receiving, through the first input/output interface, information produced by the electrical impedance monitor about electrical impedance of the myocardial infraction region; and sending, through the second input/output interface, commands that control production of the stimulating electrical signals by the electrical tissue stimulator based on the received information.

11. The implantable device of claim 1, wherein a second implantable device is configured to emit electricity of amplitude greater than subthreshold amplitude, and wherein the implantable device comprises at least a circuit of the second implantable device that has been adapted to produce at least one of the stimulating electrical signals and the monitoring electrical signals.

12. The implantable device of claim 1, wherein the implantable device comprises at least a portion of another implantable device that has been reprogrammed from emitting electricity capable of evoking an electrical pacing response to emitting subthreshold electricity that comprises at least one of the stimulating electrical signals and the monitoring electrical signals.

13. An implantable device for treating a myocardial infarction region of a myocardium, the implantable device comprising:

an implantable housing comprising at least one electrical port;

at least one electrical lead comprising at least one distal end that is fastenable to said myocardial infarction region; and at least two distal electrodes that comprise a cathode electrode and an anode electrode, wherein the at least one electrical lead is electrically coupled to the at least one electrical port and is sized to extend from the at least one electrical port to the myocardial infarction region;

an electrical tissue stimulator disposed in the implantable housing and electrically coupled to the at least one electrical port, wherein the electrical tissue stimulator is configured to produce subthreshold stimulating electrical signals for transmission over the at least one electrical lead and propagation through the myocardial infarction region for thickening or arresting thinning of the myocardial infarction region;

an electrical impedance monitor disposed in the implantable housing and electrically coupled to the at least one electrical port, wherein the electrical impedance monitor is configured to:

produce monitoring electrical signals for transmission over the at least one electrical lead and propagation through the myocardial infarction region, wherein the monitoring electrical signals are subthreshold and comprise a specified voltage and a current correlating with electrical impedance of the myocardial infarction region; and process the monitoring electrical signals to assess electrical impedance of the myocardial infarction region in accordance with the current of the monitoring electrical signals, wherein a decrease in electrical impedance is indicative of thickening or arresting thinning of the myocardial infarction region attributable to said propagation of the subthreshold stimulating electrical signals through the myocardial infarction region; and a controller disposed in the implantable housing and comprising:

a first input/output interface electrically coupled to the electrical impedance monitor;

a second input/output interface electrically coupled to the electrical tissue stimulator;

a processor; and non-transitory memory and instructions stored thereon, that when executed by the processor, cause autonomous performance of a method that comprises:

receiving, through the first input/output interface, input from the electrical impedance monitor about electrical impedance of the myocardial infraction region; and sending, through the second input/output interface, output to the electrical tissue stimulator that controls production of the subthreshold stimulating electrical signals based on the received input from the electrical impedance monitor about electrical impedance of the myocardial infraction region.

14. The implantable device of claim 13, wherein the monitoring electrical signals comprise sinusoidal signals, wherein frequency of the monitoring electrical signals is in a range of 0.5 kilohertz to 1,000 kilohertz, and wherein the current comprises a peak current in a range of 0.1 milliamps to 15 milliamps.

15. The implantable device of claim 13, wherein the specified voltage of the monitoring electrical signals comprises a peak amplitude of voltage that has been set, wherein the current of the monitoring electrical signals comprises an amplitude that varies according to change in electrical impedance of the myocardial infarction region, and wherein the method further comprises determining whether to instruct the electrical tissue stimulator to produce stimulating electrical signals for propagation through the myocardial infarction region based on change in the amplitude of the current of the monitoring electrical signal.

16. The implantable device of claim 13, wherein the implantable device comprises at least a portion of another implantable device that has been reprogrammed from producing electricity intended to evoke an electrical pacing response to producing subthreshold electricity that comprises at least one of the subthreshold stimulating electrical signals and the monitoring electrical signals.

17. An implantable device for treating a myocardial infarction region of a myocardium, the implantable device comprising:

an implantable housing;

at least one electrical lead comprising a distal end attachable to the myocardial infarction region, and a proximal end electrically coupled to the implantable housing;

an electrical tissue stimulator disposed in the implantable housing and configured to produce subthreshold stimulating electrical signals for transmission to the myocardial infarction region over the at least one electrical lead, wherein the subthreshold stimulating electrical signals are intended to thicken or arrest thinning of the myocardial infarction region;

an electrical impedance monitor disposed in the implantable housing and configured to:

produce, for transmission to the myocardial infarction region over the at least one electrical lead, subthreshold monitoring electrical signals that comprise a specified current and a voltage that correlates with electrical impedance of the myocardial infarction region; and process the subthreshold monitoring electrical signals to assess electrical impedance of the myocardial infarction region in accordance with the voltage of the subthreshold monitoring electrical signals.

18. The implantable device of claim 17, wherein frequency of the subthreshold monitoring electrical signals is in a range of 0.5 kilohertz to 1,000 kilohertz, and wherein peak current of the subthreshold monitoring electrical signals in a range of 0.1 milliamps to 15 milliamps.

19. The implantable device of claim 17, further comprising a controller disposed in the implantable housing and electrically coupled to the electrical impedance monitor and the electrical tissue monitor, the controller comprising non-transitory memory and instructions stored thereon, that when executed by the controller, cause performance of a method that comprises:

receiving input from the electrical impedance monitor about electrical impedance of the myocardial infraction region; and sending output to the electrical tissue stimulator that controls production of the subthreshold stimulating electrical signals based on the received input.

20. The implantable device of claim 17, wherein the implantable device comprises at least a portion of another implantable device that has been reprogrammed from producing electricity intended to evoke an electrical pacing response to producing subthreshold electricity that comprises at least one of the subthreshold stimulating electrical signals and the subthreshold monitoring electrical signals.

* * * * *